(12) United States Patent
Vakkalanka et al.

(10) Patent No.: US 9,790,224 B2
(45) Date of Patent: Oct. 17, 2017

(54) DUAL SELECTIVE PI3 DELTA AND GAMMA KINASE INHIBITORS

(71) Applicant: Rhizen Pharmaceuticals SA, La Chaux-de-Fonds (CH)

(72) Inventors: Swaroop K. V. S. Vakkalanka, La Chaux-de-Fonds (CH); Prashant K. Bhavar, Hyderabad (IN); Srikant Viswanadha, Hyderabad (IN); Govindarajulu Babu, Hyderabad (IN)

(73) Assignee: RHIZEN PHARMACEUTICALS SA, La Chaux-de-Fonds (CH)

( * ) Notice: Subject to any disclaimer, the term of this patent is extended or adjusted under 35 U.S.C. 154(b) by 53 days.

(21) Appl. No.: 14/295,875

(22) Filed: Jun. 4, 2014

(65) Prior Publication Data

US 2014/0364447 A1    Dec. 11, 2014

(30) Foreign Application Priority Data

Jun. 7, 2013   (IN) .......................... 2501/CHE/2013
Dec. 3, 2013   (IN) .......................... 5567/CHE/2013

(51) Int. Cl.
*A61K 31/52* (2006.01)
*C07D 473/34* (2006.01)
*A61K 45/06* (2006.01)
*C07D 473/04* (2006.01)

(52) U.S. Cl.
CPC ............ *C07D 473/34* (2013.01); *A61K 31/52* (2013.01); *A61K 45/06* (2013.01); *C07D 473/04* (2013.01)

(58) Field of Classification Search
CPC .............................. A61K 31/52; C07D 473/34
See application file for complete search history.

(56) References Cited

U.S. PATENT DOCUMENTS

2011/0118257 A1   5/2011   Muthuppalaniappan et al.
2012/0157430 A1   6/2012   Li et al.
2012/0289496 A1   11/2012  Nagarathnam et al.

FOREIGN PATENT DOCUMENTS

CH   WO 2011055215 A2 *  5/2011  ........... C07D 311/36
WO   WO-2011055215 A2    5/2011
WO   WO-2012151525 A1    11/2012

OTHER PUBLICATIONS

Navigating Cancer. "List of Cancer Chemotherapy Drugs." (c) 2013. Available from: < https://www.navigatingcancer.com/library/all/chemotherapy_drugs >.*
Kurtz, J., et al. PI3 Kinase Inhibitors in the Clinic: An Update. AntiCancer Research. (2012), vol. 32, pp. 2463-2470.*
WebMD. "Leukemia-Prevention." (c) Nov. 2014. Available from: < http://www.webmd.com/cancer/tc/leukemia-prevention >.*

* cited by examiner

*Primary Examiner* — Noble Jarrell
*Assistant Examiner* — John S Kenyon
(74) *Attorney, Agent, or Firm* — Blank Rome LLP

(57) ABSTRACT

The present invention relates to dual delta (δ) and gamma (γ) PI3K protein kinase modulators, methods of preparing them, pharmaceutical compositions containing them and methods of treatment, prevention and/or amelioration of Pi3K kinase mediated diseases or disorders with them.

32 Claims, 11 Drawing Sheets

DUAL SELECTIVE PI3 DELTA AND GAMMA KINASE INHIBITORS

The present application claims the benefit of Indian Patent Application Nos. 2501/CHE/2013, filed Jun. 7, 2013, and 5567/CHE/2013, filed Dec. 3, 2013 each of which is hereby incorporated by reference in its entirety.

FIELD OF THE INVENTION

The present invention provides dual delta (δ) and gamma (γ) PI3K protein kinase modulators, methods of preparing them, pharmaceutical compositions containing them and methods of treatment, prevention and/or amelioration of Pi3K kinase mediated diseases or disorders with them.

BACKGROUND OF THE INVENTION

Phosphoinositide-3 kinase (PI3K) belongs to a class of intracellular lipid kinases that phosphorylate the 3 position hydroxyl group of the inositol ring of phosphoinositide lipids (PIs) generating lipid second messengers. While alpha and beta isoforms are ubiquitous in their distribution, expression of delta and gamma is restricted to circulating hematogenous cells and endothelial cells. Unlike PI3K-alpha or beta, mice lacking expression of gamma or delta do not show any adverse phenotype indicating that targeting of these specific isoforms would not result in overt toxicity.

Recently, targeted inhibitors of the phosphoinositide-3-kinase (PI3K) pathway have been suggested as immunomodulatory agents. This interest stems from the fact that the PI3K pathway serves multiple functions in immune cell signaling, primarily through the generation of phosphatidylinositol (3,4,5)-trisphosphate (PIP3), a membranebound second messenger. PIP3 recruits proteins to the cytoplasmic side of the lipid bilayer, including protein kinases and GTPases, initiating a complex network of downstream signaling cascades important in the regulation of immune cell adhesion, migration, and cell-cell communication.

The four class I PI3K isoforms differ significantly in their tissue distribution. PI3Kα and PI3Kβ are ubiquitous and activated downstream of receptor tyrosine kinases (RTK), whereas PI3K δ and PI3K γ are primarily limited to hematopoietic and endothelial cells, and are activated downstream of RTKs, and G protein coupled receptors (GPCR) respectively. Mouse genetic studies have revealed that PI3Kα and PI3Kβ are essential for normal development, whereas loss of PI3K δ and/or PI3K γ yields viable offspring with selective immune deficits.

The expression pattern and functions of PI3K δ and PI3K γ have generated much interest in developing PI3Kδ/γ inhibitors as agents for many diseases, including rheumatoid arthritis, allergies, asthma, chronic obstructive pulmonary disease and multiple sclerosis (Hirsch et al., *Pharmacol. Ther.*, 118, 192-205, 2008; Marone et al., *Biochim. Biophys. Acta.*, 1784, 159-185, 2008; Rommel et al., *Nat. Rev. Immunol.*, 7, 191-201, 2007; Ruckle et al., *Nat. Rev. Drug Discov.*, 5, 903-918, 2006). Studies using both pharmacologic and genetic methods have shown these two isoforms often demonstrate synergistic interactions with each other (Konrad et al., *J. Biol. Chem.*, 283, 33296-33303, 2008; Laffargue et al., *Immunity*, 16, 441-451, 2002). In mast cells, for example, PI3Kδ is essential for degranulation in response to IgE cross-linking of Fc-receptors (Ali et al., *J. Immunol.*, 180, 2538-2544, 2008), but PI3Kγ plays an important role in amplifying the response (Laffargue et al., *Immunity*, 16, 441-451, 2002). Similar effects have been seen in other cellular functions, including lymphocyte homing and the neutrophil respiratory burst where PI3Kγ plays a critical role and PI3Kδ amplifies each process. The nonredundant but related roles of PI3Kδ and PI3Kγ have made it difficult to determine which of the two isoforms (alone or in combination) is best targeted in a particular inflammatory disorder. Studies using mice that lack PI3Kδ and/or PI3Kγ or express kinase-dead variants of PI3Kδ and PI3Kγ have been valuable tools in understanding their roles. For example, PI3Kδ knockout mice demonstrated diminished neutrophil chemotaxis, diminished antibody production (both T cell dependent and independent) (Jou et al., *Mol. Cell. Biol.*, 22, 8580-8591, 2002), and lower numbers of mature B cells (Clayton et al., *J. Exp. Med.*, 196, 753-763, 2002; Jou et al., *Mol. Cell. Biol.*, 22, 8580-8591, 2002), and a decrease in their proliferation in response to anti-IgM (Jou et al., 2002). This phenotype was replicated in the PI3Kδ kinase-dead variant and with PI3Kδ selective inhibitors along with decreased numbers of and proliferation of mast cells, and an attenuated allergic response. The PI3Kγ knockout contained higher numbers of, but less responsive, neutrophils, lower numbers of and less responsive macrophages and dendritic cells displayed decreased mast cell degranulation (Laffargue et al., 2002), a higher ratio of CD4+ to CD8+ T cells), increased thymocyte apoptosis, diminished induction of CXCR3 on activated T cells and decreased cardiac contractility. This latter effect on cardiac tissue was a concern for chronic dosing of patients with PI3Kγ inhibitors. However, this concern was largely mitigated when the PI3Kγ kinase-dead variant (which better mimics inhibition of the kinase rather than loss of the protein) showed similar immune cell phenotypes, but importantly had no cardiac defects. The cardiac effect was later shown to be due to scaffolding effects rather than the catalytic activity of PI3Kγ. The dual PI3Kδ/PI3Kγ knockout was viable but exhibited serious defects in T cell development and thymocyte survival. The PI3Kγ knockout/PI3Kδ kinase-dead combination produced a similar phenotype suggesting that at least within the immune system, the role of PI3Kδ is likely only a catalytic one. Interpretation of studies using knockout and kinase-dead mice can be challenging because these models provide only a steady-state picture of the immune system, lack temporal and dose control, and do not permit a full understanding of how a dynamic immune response will react to reversible inhibition. Selective inhibitors with varying profiles (PI3Kδ, PI3Kγ, and PI3Kδ/γ) are necessary for studies of leukocyte signaling in order to assess the relative contributions of each PI3K to immune cell activation (Olusegon et al., *Chemistry & Biology*, 1, 123-134 (2010), including the references cited therein)

Dual inhibition of δ/γ is strongly implicated as an intervention strategy in allergic and non-allergic inflammation of the airways and other autoimmune diseases. Scientific evidence for PI3K-δ and γ gamma involvement in various cellular processes underlying asthma and COPD stems from inhibitor studies and gene-targeting approaches. Also, resistance to conventional therapies such as corticosteroids in several COPD patients has been attributed to an up-regulation of the PI3K δ/γ pathway. Disruption of PI3K-δ/γ signalling therefore provides a novel strategy aimed at counteracting the immuno-inflammatory response. Due to the pivotal role played by PI3K-δ and γ in mediating inflammatory cell functionality such as leukocyte migration and activation, and mast cell degranulation, blocking these isoforms may also be an effective strategy for the treatment of rheumatoid arthritis as well. Given the established criticality of these isoforms in immune surveillance, inhibitors specifically targeting the δ and γ isoforms would be expected to attenuate the progression of immune response encountered in airway inflammation and rheumatoid arthritis (William et. al *Chemistry & Biology*, 17, 123-134, 2010 and Thompson, et al. *Chemistry & Biology*, 17:101-102, 2010)

Reviews and studies regarding PI3K and related protein kinase pathways have been given by Liu et. al., *Nature Reviews Drug Discovery*, 8, 627-644, 2009); Nathan T. et. al., *Mol Cancer Ther.*, 8(1), 2009; Marone et, al., *Biochimica et Biophysica Acta*, 1784, 159-185, 2008 and Markman et. al., *Annals of Oncology Advance Access*, published August 2009. Similarly reviews and studies regarding role of PI3K δ and γ have been given by William et. al., *Chemistry & Biology*, 17, 123-134, 2010 and Timothy et. al. *J. Med. Chem.*, 55 (20), 8559-8581, 2012. All of these literature disclosures are hereby incorporated by reference in their entirety.

Compounds such as IPI-145 and CAL130 have been reported as dual inhibitors of Pi3K δ/γ. IPI-145 is under clinical investigation for cancer, asthma and rheumatoid arthritis. IPI-45 have been reported to have a maximum tolerated dose (MTD) of 75 mg BID (55th ASH® Annula Meeting New Orleans-LA, Dec. 7-10, 2013). There are no reports of CAL-130 being investigated for clinical purposes.

There still remains an unmet need for dual δ γ PI3K modulators for the treatment of diseases and disorders associated with δ/γ PI3K kinases-mediated events.

Further reference is made herein to International Publication Nos. WO 11/055,215 and WO 12/151,525 and U.S. Publication Nos. 2011/0118257 and 2012/0289496, each of which is incorporated herein by reference in its entirety.

SUMMARY OF THE INVENTION

The present invention is directed to selective dual inhibitors of PI3K delta and gamma protein kinases. These compounds are suitable for use in a pharmaceutical composition for the treatment of a PI3K associated disease, disorder or condition, e.g., a proliferative disease such as cancer Inhibition of both PI3K delta and gamma protein kinases may provide beneficial effects in the treatment of certain diseases and disorders.

The selective dual inhibitors of the present invention include the following compounds, pharmaceutically acceptable salts thereof, and prodrugs thereof:
(RS)-2-(1-(9H-purin-6-ylamino)propyl)-3-(3-fluorophenyl)-4H-chromen-4-one. (Compound A)
(S)-2-(1-(9H-purin-6-ylamino)propyl)-3-(3-fluorophenyl)-4H-chromen-4-one. (Compound A1)
(R)-2-(1-(9H-purin-6-ylamino)propyl)-3-(3-fluorophenyl)-4H-chromen-4-one. (Compound A2)

The chemical structures of the compounds of the present invention are shown below.

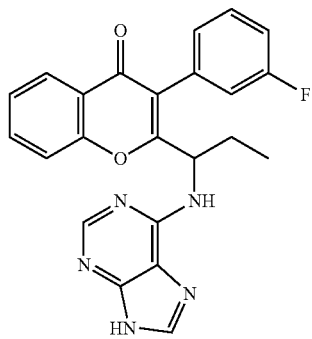

(A)

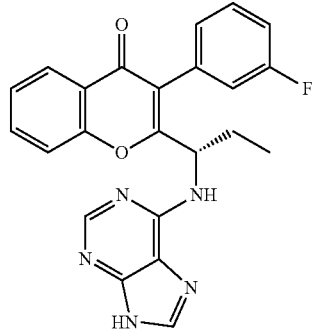

(A1)

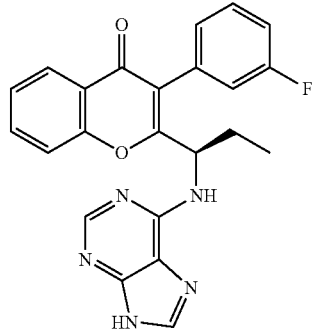

(A2)

In one embodiment, the present invention relates to the compound (S)-2-(1-(9H-purin-6-ylamino)propyl)-3-(3-fluorophenyl)-4H-chromen-4-one, or a pharmaceutically acceptable salt thereof.

In one embodiment, the compound (S)-2-(1-(9H-purin-6-ylamino)propyl)-3-(3-fluorophenyl)-4H-chromen-4-one, or a pharmaceutically acceptable salt thereof, is substantially free (e.g., contains less than about 10%, such as less than about 5%, less than about 2.5%, less than about 1%, less than about 0.1% by weight or is free) of (R)-2-(1-(9H-purin-6-ylamino)propyl)-3-(3-fluorophenyl)-4H-chromen-4-one and pharmaceutically acceptable salts thereof.

In another embodiment, the compound (S)-2-(1-(9H-purin-6-ylamino)propyl)-3-(3-fluorophenyl)-4H-chromen-4-one, or a pharmaceutically acceptable salt thereof, has an enantiomeric excess of greater than about 90%, such as greater than about 91%, greater than about 92%, greater than about 93%, greater than about 94%, greater than about 95%, greater than about 96%, greater than about 97%, greater than about 98%, greater than about 99%, greater than about 99.5%, greater than about 99.9%, or greater than about 99.99%.

In one preferred embodiment, the present invention relates to the compound (S)-2-(1-(9H-purin-6-ylamino)propyl)-3-(3-fluorophenyl)-4H-chromen-4-one (Compound A1).

The invention further provides a pharmaceutical composition comprising one or more compounds of the present invention (such as compound A1) together with a pharmaceutically acceptable carrier. The pharmaceutical composition may further comprise one or more of additional active agents (such as anti-cancer agents and the active agents discussed below). In one embodiment, the pharmaceutical composition includes a therapeutically effective amount of one or more compounds of the present invention.

Another embodiment is a method of inhibiting PI3K delta and gamma in a patient by administering to the patient an effective amount of at least one compound of the present invention.

Yet another embodiment is a method of treating, preventing, and/or inhibiting a PI3K protein kinase mediated disease, disorder or condition (such as cancer or other proliferative disease or disorder) in a patient by administering to the patient an effective amount of at least one compound of the present invention.

Yet another embodiment of the present invention is a method for inhibiting PI3K, in particular PI3K delta and gamma kinase in a patient by administering to the patient an effective amount of at least one compound of the present invention.

Yet another embodiment of the present invention is a method for treating an inflammatory, autoimmune or proliferative disease via modulation of a protein kinase (such as PI3 delta and gamma kinase) by administering to a patient in need of such treatment an effective amount of at least one compound of the present invention. In one embodiment, the compound of the present invention inhibits both the PI3K delta and gamma protein kinase.

Yet another embodiment of the present invention is a method for treating an inflammatory, autoimmune or proliferative disease via modulation of a protein kinase (such as PI3 delta and gamma kinase) by administering to a patient in need of such treatment an effective amount of at least one compound of the present invention, in combination (simultaneously or sequentially) with at least one other anti-inflammatory, immunomodulator or anti-cancer agent (or a combination thereof). In one embodiment, the compound of the present invention inhibits both the PI3K delta and gamma protein kinase.

The compounds of the present invention are useful in the treatment of a variety of cancers, including, but not limited to:

carcinoma, including, but not limited to, that of the bladder, breast, colon, kidney, liver, lung, including small cell lung cancer, esophagus, gall bladder, ovary, pancreas, stomach, cervix, thyroid, prostate, and skin, including squamous cell carcinoma;

hematopoietic tumors of lymphoid lineage, including, but not limited to, leukemia, acute lymphocytic leukemia, acute lymphoblastic leukemia, B-cell lymphoma, T-cell lymphoma, Hodgkin's lymphoma, non-Hodgkins lymphoma, hairy cell lymphoma and Burkett's lymphoma;

hematopoietic tumors of myeloid lineage, including, but not limited to, acute and chronic myelogenous leukemias, myelodysplastic syndrome and promyelocytic leukemia;

tumors of mesenchymal origin, including, but not limited to, fibrosarcoma and rhabdomyosarcoma;

tumors of the central and peripheral nervous system, including, but not limited to, astrocytoma, neuroblastoma, glioma and schwannomas; and other tumors, including, but not limited to, melanoma, seminoma, teratocarcinoma, osteosarcoma, xenoderoma pigmentosum, keratoctanthoma, thyroid follicular cancer and Kaposi's sarcoma.

In one embodiment, the compounds of the present invention are administered to treat a leukemia, acute lymphocytic leukemia, acute lymphoblastic leukemia, B-cell lymphoma, T-cell lymphoma, Hodgkin's lymphoma, non-Hodgkins lymphoma, hairy cell lymphoma, Burkett's lymphoma, acute and chronic myelogenous leukemias, myelodysplastic syndrome and promyelocytic leukemia.

Due to the key role of protein kinases in the regulation of cellular proliferation in general, the protein kinase inhibitors of the present invention could act as reversible cytostatic agents, and may be useful therefore in the treatment of any disease process which features abnormal cellular proliferation, e.g., benign prostatic hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

The compounds of the present invention as modulators of apoptosis are useful in the treatment of cancer (including but not limited to those types mentioned herein above), viral infections (including, but not limited to, herpevirus, poxvirus, Epstein-Barr virus, Sindbis virus and adenovirus), autoimmune diseases (including, but not limited, to systemic lupus, erythematosus, autoimmune mediated glomerulonephritis, rheumatoid arthritis, psoriasis, inflammatory bowel disease, and autoimmune diabetes mellitus), neurodegenerative disorders (including, but not limited to, Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including, but not limited to, chronic anemia and aplastic anemia), degenerative diseases of the musculoskeletal system (including, but not limited to, osteoporosis and arthritis) aspirin-sensitive rhinosinusitis, cystic fibrosis, multiple sclerosis, kidney diseases and cancer pain. The compounds of the present invention are also useful in the prevention, inhibition, or suppression of AIDS development in HIV-infected individuals.

The compounds of the present invention can modulate the level of cellular RNA and DNA synthesis. These agents are therefore useful in the treatment of viral infections, including, but not limited to, HIV, human papilloma virus, herpesvirus, poxvirus, Epstein-Barr virus, Sindbis virus and adenovirus.

The compounds of the present invention are useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse. The compounds of the present invention are also useful in inhibiting tumor angiogenesis and metastasis. One embodiment of the invention is a method of inhibiting tumor angiogenesis or metastasis in a patient in need thereof by administering an effective amount of one or more compounds of the present invention.

Another embodiment of the present invention is a method of treating an immune system-related disease (e.g., an autoimmune disease), a disease or disorder involving inflammation (e.g., asthma, chronic obstructive pulmonary disease (COPD), rheumatoid arthritis, inflammatory bowel disease, glomerulonephritis, neuroinflammatory diseases, multiple sclerosis, uveitis and disorders of the immune system), cancer or other proliferative disease, a hepatic disease or disorder, a renal disease or disorder. The method includes administering an effective amount of one or more compounds of the present invention.

Examples of immune disorders include, but are not limited to, psoriasis, rheumatoid arthritis, vasculitis, inflammatory bowel disease, dermatitis, osteoarthritis, asthma, inflammatory muscle disease, allergic rhinitis, vaginitis, interstitial cystitis, scleroderma, osteoporosis, eczema, allogeneic or xenogeneic transplantation (organ, bone marrow, stem cells and other cells and tissues) graft rejection, graft-versus-host disease, lupus erythematosus, inflammatory disease, type I diabetes, pulmonary fibrosis, dermatomyositis, Sjogren's syndrome, thyroiditis (e.g., Hashimoto's and autoimmune thyroiditis), myasthenia gravis, autoimmune hemolytic anemia, multiple sclerosis, cystic fibrosis, chronic relapsing hepatitis, primary biliary cirrhosis, allergic conjunctivitis and atopic dermatitis.

In one embodiment, the compounds described herein are useful as immunosuppressants to prevent transplant graft rejections, allogeneic or xenogeneic transplantation rejection (organ, bone marrow, stem cells, other cells and tissues), and graft-versus-host disease. In other embodiments, transplant graft rejections result from tissue or organ transplants. In further embodiments, graft-versus-host disease results from bone marrow or stem cell transplantation. One embodiment is a method of preventing or decreasing the risk of transplant graft rejection, allogeneic or xenogeneic transplantation rejection (organ, bone marrow, stem cells, other cells and tissues), or graft-versus-host disease by administering an effective amount of one or more compounds of the present invention.

The compounds of the present invention are also useful in combination (administered together or sequentially) with known anti-cancer treatments, such as radiation therapy or with cytostatic or cytotoxic or anticancer agents, such as, for example, DNA interactive agents, such as cisplatin or doxorubicin; topoisomerase II inhibitors, such as etoposide; topoisomerase I inhibitors such as CPT-11 or topotecan; tubulin interacting agents, such as paclitaxel, docetaxel or the epothilones (for example ixabepilone), either naturally occurring or synthetic; hormonal agents, such as tamoxifen; thymidilate synthase inhibitors, such as 5-fluorouracil; and anti-metabolites, such as methotrexate, other tyrosine kinase inhibitors such as Iressa and OSI-774; angiogenesis inhibitors; EGF inhibitors; VEGF inhibitors; CDK inhibitors; SRC inhibitors; c-Kit inhibitors; Her1/2 inhibitors and monoclonal antibodies directed against growth factor receptors such as erbitux (EGF) and herceptin (Her2) and other protein kinase modulators as well.

The compounds of the present invention are also useful in combination (administered together or sequentially) with one or more steroidal anti-inflammatory drugs, non-steroidal anti-inflammatory drugs (NSAIDs) or immune selective anti-inflammatory derivatives (ImSAIDs).

The invention further provides a pharmaceutical composition comprising one or more compounds of the present invention together with a pharmaceutically acceptable carrier. The pharmaceutical composition may further comprise one or more of the active ingredients identified above, such as other anti-cancer agents.

Yet another embodiment is a method of treating leukemia in a patient in need thereof by administering a therapeutically effective amount of a compound of the present invention. For example, the compounds of the present invention are effective for treating chronic lymphocytic leukemia (CLL), non-Hodgkin lymphoma (NHL), Hodgkin lymphoma (HL) acute myeloid leukemia (AML), multiple myeloma (MM), small lymphocytic lymphoma (SLL), and indolent non-Hodgkin's lymphoma (I-NHL).

Yet another embodiment is a method of treating leukemia in a patient in need thereof by administering a therapeutically effective amount of a compound of the present invention. For example, the compounds of the present invention are effective for treating autoimmune disorders such as asthma, COPD, rhematoid arthritis, psorias, lupus and experimental autoimmune encephalomyelitis (EAE).

Yet another embodiment is a method of treating allergic rhinitis in a patient in need thereof by administering a therapeutically effective amount of a compound of the present invention.

DETAILED DESCRIPTION OF THE INVENTION

Figure 1:
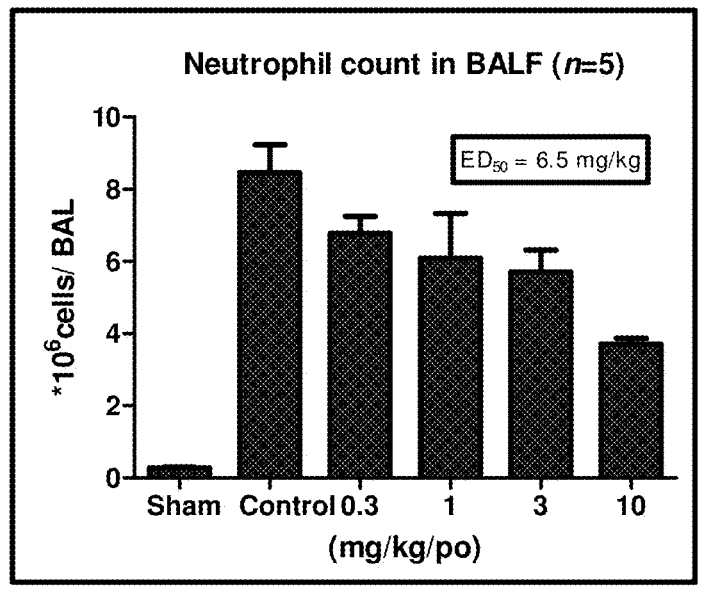
FIG. 1 depicts a bar graph of the neutrophil count in bronchioalveolar lavage fluid (BALF) from animals treated with 0, 0.3, 1, 3, and 10 mg/kg of Compound A1 (po) according to the Lipopolysaccharide induced pulmonary neutrophilia model described in Assay 7.

As used herein the following definitions shall apply unless otherwise indicated. Further many of the groups defined herein can be optionally substituted. The listing of substituents in the definition is exemplary and is not to be construed to limit the substituents defined elsewhere in the specification.

Certain of the compounds described herein contain one or more asymmetric centers and can thus give rise to enantiomers, diastereomers, and other stereoisomeric forms that can be defined, in terms of absolute stereochemistry, as (R)- or (S)-. Unless otherwise specified, the present chemical entities, pharmaceutical compositions and methods are meant to include all such possible isomers, including racemic mixtures, optically pure forms and intermediate mixtures. For the instance, non-limiting example of intermediate mixtures include a mixture of R:S or S:R isomers in a ratio of 10:90, 13:87, 17:83, 20:80, or 22:78. Optically active (R)- and (S)-isomers can be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers.

The term "tautomers" refers to compounds, which are characterized by relatively easy interconversion of isomeric forms in equilibrium. These isomers are intended to be covered by this invention. "Tautomers" are structurally distinct isomers that interconvert by tautomerization. "Tautomerization" is a form of isomerization and includes prototropic or proton-shift tautomerization, which is considered a subset of acid-base chemistry. "Prototropic tautomerization" or "proton-shift tautomerization" involves the migration of a proton accompanied by changes in bond order, often the interchange of a single bond with an adjacent double bond. Where tautomerization is possible (e.g. in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

The term "prodrug" refers to a compound, which is an inactive precursor of a compound that is converted into its active form in the body by normal metabolic processes. Prodrug design is discussed generally in Hardma, et al. (Eds.), Goodman and Gilman's The Pharmacological Basis of Therapeutics, 9th ed., pp. 11-16 (1996). A thorough discussion is provided in Higuchi, et al., Prodrugs as Novel Delivery Systems, Vol. 14, ASCD Symposium Series, and in Roche (ed.), Bioreversible Carriers in Drug Design, American Pharmaceutical Association and Pergamon Press (1987). To illustrate, prodrugs can be converted into a pharmacologically active form through hydrolysis of, for example, an ester or amide linkage, thereby introducing or exposing a functional group on the resultant product. The prodrugs can be designed to react with an endogenous compound to form a water-soluble conjugate that further enhances the pharmacological properties of the compound, for example, increased circulatory half-life. Alternatively, prodrugs can be designed to undergo covalent modification on a functional group with, for example, glucuronic acid, sulfate, glutathione, amino acids, or acetate. The resulting conjugate can be inactivated and excreted in the urine, or rendered more potent than the parent compound. High molecular weight conjugates also can be excreted into the bile, subjected to enzymatic cleavage, and released back into the circulation, thereby effectively increasing the biological half-life of the originally administered compound.

The term "ester" refers to a compound, which is formed by reaction between an acid and an alcohol with elimination of water. An ester can be represented by the general formula RCOOR' (where R is a drug and R' is a chemical group).

These prodrugs and esters are intended to be covered within the scope of this invention.

Additionally the instant invention also includes the compounds which differ only in the presence of one or more isotopically enriched atoms for example replacement of hydrogen with deuterium or tritium, or the replacement of a carbon by $^{13}C$- or $^{14}C$-enriched carbon.

The compounds of the present invention may also contain unnatural proportions of atomic isotopes at one or more of atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are encompassed within the scope of the present invention.

Pharmaceutically acceptable salts forming part of this invention include salts derived from inorganic bases such as Li, Na, K, Ca, Mg, Fe, Cu, Zn, and Mn; salts of organic bases such as N,N'-diacetylethylenediamine, glucamine, triethylamine, choline, hydroxide, dicyclohexylamine, metformin, benzylamine, trialkylamine, and thiamine; chiral bases such as alkylphenylamine, glycinol, and phenyl glycinol; salts of natural amino acids such as glycine, alanine, valine, leucine, isoleucine, norleucine, tyrosine, cystine, cysteine, methionine, proline, hydroxy proline, histidine, ornithine, lysine, arginine, and serine; quaternary ammonium salts of the compounds of invention with alkyl halides, alkyl sulphates such as MeI and $(Me)_2SO_4$; non-natural amino acids such as D-isomers or substituted amino acids; guanidine; and substituted guanidine wherein the substituents are selected from nitro, amino, alkyl, alkenyl, alkynyl, ammonium or substituted ammonium salts and aluminum salts. Salts may include acid addition salts where appropriate which may be sulphates, nitrates, phosphates, perchlorates, borates, hydrohalides, acetates, tartrates, maleates, citrates, fumarates, succinates, palmoates, methanesulphonates, benzoates, salicylates, benzenesulfonates, ascorbates, glycerophosphates, and ketoglutarates.

When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary from, for example, between 1% and 15% of the stated number or numerical range. The term "comprising" (and related terms such as "comprise" or "comprises" or "having" or "including") includes those embodiments, for example, an embodiment of any composition of matter, composition, method, or process, or the like, that "consist of" or "consist essentially of" the described features.

The following abbreviations and terms have the indicated meanings throughout: PI3-K=Phosphoinositide 3-kinase; PI=phosphatidylinositol; AIDS=Acquired Immuno Deficiency Syndrome; HIV=Human Immunodeficiency Virus; MeI=Methyl Iodide; ND: Not determined.

Abbreviations used herein have their conventional meaning within the chemical and biological arts.

The term "cell proliferation" refers to a phenomenon by which the cell number has changed as a result of division. This term also encompasses cell growth by which the cell morphology has changed (e.g., increased in size) consistent with a proliferative signal.

The terms "co-administration," "administered in combination with," and their grammatical equivalents, as used herein, encompass administration of two or more agents to an animal so that both agents and/or their metabolites are present in the animal at the same time. Co-administration includes simultaneous administration in separate compositions, administration at different times in separate compositions, or administration in a composition in which both agents are present.

The term "effective amount" or "therapeutically effective amount" refers to that amount of a compound described herein that is sufficient to effect the intended application including but not limited to disease treatment, as defined below. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g. reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried.

As used herein, "treatment," "treating," or "ameliorating" are used interchangeably. These terms refers to an approach for obtaining beneficial or desired results including but, not limited to, therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "subject" or "patient" refers to an animal (e.g., a dog, cat, horse, or pig), such as a mammal, for example a human. The methods described herein can be useful in both human therapeutics and veterinary applications. In some embodiments, the patient is a mammal, and in some embodiments, the patient is human.

"Radiation therapy" means exposing a patient, using routine methods and compositions known to the practitioner, to radiation emitters such as alpha-particle emitting radionuclides (e.g., actinium and thorium radionuclides), low linear energy transfer (LET) radiation emitters (i.e. beta emitters), conversion electron emitters (e.g. strontium-89 and samarium-153-EDTMP), or high-energy radiation, including, without limitation, x-rays, gamma rays, and neutrons.

"Signal transduction" is a process during which stimulatory or inhibitory signals are transmitted into and within a cell to elicit an intracellular response. A modulator of a signal transduction pathway refers to a compound which modulates the activity of one or more cellular proteins mapped to the same specific signal transduction pathway. A modulator may augment (agonist) or suppress (antagonist) the activity of a signaling molecule.

The term "selective inhibition" or "selectively inhibit" as applied to a biologically active agent refers to the agent's ability to selectively reduce the target signaling activity as compared to off-target signaling activity, via direct or indirect interaction with the target.

The term "pharmaceutically acceptable carrier" or "pharmaceutically acceptable excipient" includes, but is not limited to, any and all solvents, dispersion media, coatings, antibacterial and antifungal agents, isotonic and absorption delaying agents, one or more suitable diluents, fillers, salts, disintegrants, binders, lubricants, glidants, wetting agents, controlled release matrices, colorants/flavoring, carriers, excipients, buffers, stabilizers, solubilizers, and combinations thereof. Except insofar as any conventional media or agent is incompatible with the active ingredient, its use in the therapeutic compositions of the invention is contemplated. Supplementary active ingredients can also be incorporated into the compositions.

In certain embodiments, one or more of the compounds described herein bind specifically to a PI3 kinase or a protein kinase selected from the group consisting of mTor, DNA-dependent protein kinase (Pubmed protein accession number (PPAN) AAA79184), AbI tyrosine kinase (CAA52387), Bcr-Abl, hemopoietic cell kinase (PPAN CAI19695), Src (PPAN CAA24495), vascular endothelial growth factor receptor 2 (PPAN ABB82619), epidermal growth factor receptor (PPAN AG43241), EPH receptor B4 (PPAN EAL23820), stem cell factor receptor (PPAN AAF22141), Tyrosine-protein kinase receptor TIE-2 (PPAN Q02858), fms-related tyrosine kinase 3 (PPAN NP_004110), platelet-derived growth factor receptor alpha (PPAN NP_990080), RET (PPAN CAA73131), and any other related protein kinases, as well as any functional mutants thereof.

In other embodiments, the $IC_{50}$ of a compound described herein for pi $10\alpha$, pi $10\beta$, pi $10\gamma$, or pi $10\delta$ is less than about 1 µM, less than about 100 nM, less than about 50 nM, less than about 10 nM, less than 1 nM or less than about 0.5 nM. In some embodiments, the $IC_{50}$ of a compound described herein for mTor is less than about 1 µM, less than about 100 nM, less than about 50 nM, less than about 10 nM, less than 1 nM or less than about 0.5 nM. In some other embodiments, one or more of the compounds described herein exhibit dual binding specificity and are capable of inhibiting a PI3 kinase (e.g., a class I PI3 kinase) as well as a protein kinase (e.g., mTor) with an $IC_{50}$ value less than about 1 µM, less than about 100 nM, less than about 50 nM, less than about 10 nM, less than 1 nM or less than about 0.5 nM.

In additional embodiments, the compounds of the present invention exhibit one or more functional characteristics disclosed herein. For example, one or more of the compounds described herein bind specifically to a PI3 kinase. In some embodiments, the $IC_{50}$ of a compound described herein for pi 10α, pi 10β, pi 10γ, or pi 10δ is less than about 1 μM, less than about 100 nM, less than about 50 nM, less than about 10 nM, less than about 1 nM, less than about 0.5 nM, less than about 100 pM, or less than about 50 pM.

In other embodiments, the compounds of the present invention selectively inhibit one or more members of type I or class I phosphatidylinositol 3-kinases (PI3-kinase) with an $IC_{50}$ value of about 100 nM or less, about 50 nM or less, about 10 nM or less, about 5 nM or less, about 100 pM or less, about 10 pM or less, or about 1 pM or less as measured in an in vitro kinase assay.

In yet another aspect, an inhibitor that selectively inhibits one or more members of type I PI3-kinases, or an inhibitor that selectively inhibits one or more type I PI3-kinase mediated signaling pathways, alternatively can be understood to refer to a compound that exhibits a 50% inhibitory concentration ($IC_{50}$) with respect to a given type I PI3-kinase, that is at least 10-fold lower, at least 20-fold lower, at least 50-fold lower, at least 100-fold lower, at least 1000-fold lower than the inhibitor's $IC_{50}$ with respect to the rest of the other type I PI3-kinases.

As used herein, the term "dual PI3-kinase δ/γ inhibitor" and "dual PI3-kinase δ/γ selective inhibitor" refers to a compound that inhibits the activity of both the PI3-kinase δ and γ isozyme more effectively than other isozymes of the PI3K family. A dual PI3-kinase δ/γ inhibitor is therefore more selective for PI3-kinase δ and γ than conventional PI3K inhibitors such as CAL-130, wortmannin and LY294002, which are nonselective PI3K inhibitors.

Inhibition of PI3-kinase δ and γ may be of therapeutic benefit in treatment of various conditions, e.g., conditions characterized by an inflammatory response including, but not limited to, autoimmune diseases, allergic diseases, and arthritic diseases. Importantly, inhibition of PI3-kinase δ and γ function does not appear to affect biological functions such as viability and fertility.

"Inflammatory response" as used herein is characterized by redness, heat, swelling and pain (i.e., inflammation) and typically involves tissue injury or destruction. An inflammatory response is usually a localized, protective response elicited by injury or destruction of tissues, which serves to destroy, dilute or wall off (sequester) both the injurious agent and the injured tissue. Inflammatory responses are notably associated with the influx of leukocytes and/or leukocyte (e.g., neutrophil) chemotaxis. Inflammatory responses may result from infection with pathogenic organisms and viruses, noninfectious means such as trauma or reperfusion following myocardial infarction or stroke, immune responses to foreign antigens, and autoimmune diseases. Inflammatory responses amenable to treatment with the methods and compounds according to the invention encompass conditions associated with reactions of the specific defense system as well as conditions associated with reactions of the non-specific defense system.

The therapeutic methods of the invention include methods for the amelioration of conditions associated with inflammatory cell activation. "Inflammatory cell activation" refers to the induction by a stimulus (including but not limited to, cytokines, antigens or auto-antibodies) of a proliferative cellular response, the production of soluble mediators (including but not limited to cytokines, oxygen radicals, enzymes, prostanoids, or vasoactive amines), or cell surface expression of new or increased numbers of mediators (including but not limited to, major histocompatibility antigens or cell adhesion molecules) in inflammatory cells (including but not limited to monocytes, macrophages, T lymphocytes, B lymphocytes, granulocytes (polymorphonuclear leukocytes including neutrophils, basophils, and eosinophils) mast cells, dendritic cells, Langerhans cells, and endothelial cells). It will be appreciated by persons skilled in the art that the activation of one or a combination of these phenotypes in these cells can contribute to the initiation, perpetuation, or exacerbation of an inflammatory condition.

"Autoimmune disease" as used herein refers to any group of disorders in which tissue injury is associated with humoral or cell-mediated responses to the body's own constituents.

"Transplant rejection" as used herein refers-to any immune response directed against grafted tissue (including organs or cells (e.g., bone marrow), characterized by a loss of function of the grafted and surrounding tissues, pain, swelling, leukocytosis, and thrombocytopenia).

"Allergic disease" as used herein refers to any symptoms, tissue damage, or loss of tissue function resulting from allergy.

"Arthritic disease" as used herein refers to any disease that is characterized by inflammatory lesions of the joints attributable to a variety of etiologies.

"Dermatitis" as used herein refers to any of a large family of diseases of the skin that are characterized by inflammation of the skin attributable to a variety of etiologies.

As previously described, the term "dual PI3-kinase δ/γ selective inhibitor" generally refers to a compound that inhibits the activity of the PI3-kinase δ and γ isozyme more effectively than other isozymes of the PI3K family. The relative efficacies of compounds as inhibitors of an enzyme activity (or other biological activity) can be established by determining the concentrations at which each compound inhibits the activity to a predefined extent and then comparing the results. Typically, the preferred determination is the concentration that inhibits 50% of the activity in a biochemical assay, i.e., the 50% inhibitory concentration or "$IC_{50}$". $IC_{50}$ determinations can be accomplished using conventional techniques known in the art. In general, an $IC_{50}$ can be determined by measuring the activity of a given enzyme in the presence of a range of concentrations of the inhibitor under study. The experimentally obtained values of enzyme activity then are plotted against the inhibitor concentrations used. The concentration of the inhibitor that shows 50% enzyme activity (as compared to the activity in the absence of any inhibitor) is taken as the $IC_{50}$ value. Analogously, other inhibitory concentrations can be defined through appropriate determinations of activity. For example, in some settings it can be desirable to establish a 90% inhibitory concentration, i.e., $IC_{90}$, etc.

Accordingly, a dual PI3-kinase δ/γ selective inhibitor alternatively can be understood to refer to a compound that exhibits a 50% inhibitory concentration ($IC_{50}$) with respect to PI3-kinase δ and γ, that is at least 10-fold lower, at least 20-fold lower, or at least 30-fold lower than the $IC_{50}$ value with respect to any or all of the other class I PI3K family members. In an alternative embodiment of the invention, the term dual PI3-kinase δ/γ selective inhibitor can be understood to refer to a compound that exhibits an $IC_{50}$ with respect to PI3-kinase δ and γ that is at least 30-fold lower, at least 50-fold lower, at least 100-fold lower, at least 200-fold lower, or at least 500-fold lower than the $IC_{50}$ with respect to any or all of the other PI3K class I family members. A dual PI3-kinase δ/γ selective inhibitor is typically administered in an amount such that it selectively inhibits both PI3-kinase δ and γ activity, as described above.

In certain embodiments, the compounds of the present invention exhibit PI3-kinase δ and γ inhibition almost equally (~1:1) or at a maximum ratio of 1:5, i.e., the compound the of the present invention exhibit almost equal $IC_{50}$ values for both PI3-kinase δ and γ enzyme, or at most a 3 to 8 fold difference between the two.

The methods of the invention may be applied to cell populations in vivo or ex vivo. "In vivo" means within a living individual, as within an animal or human or in a subject's body. In this context, the methods of the invention may be used therapeutically or prophylactically in an individual. "Ex vivo" or "in vitro" means outside of a living individual. Examples of ex vivo cell populations include in vitro cell cultures and biological samples including but not limited to fluid or tissue samples obtained from individuals. Such samples may be obtained by methods known in the art. Exemplary biological fluid samples include blood, cerebrospinal fluid, urine, and saliva. Exemplary tissue samples include tumors and biopsies thereof. In this context, the invention may be used for a variety of purposes, including therapeutic and experimental purposes. For example, the invention may be used ex vivo or in vitro to determine the optimal schedule and/or dosing of administration of a PI3-kinase δ selective inhibitor for a given indication, cell type, individual, and other parameters. Information gleaned from such use may be used for experimental or diagnostic purposes or in the clinic to set protocols for in vivo treatment. Other ex vivo uses for which the invention may be suited are described below or will become apparent to those skilled in the art.

The compounds of the present invention can be prepared by methods known in the art, such as those described in International Publication Nos. WO 2011/055215, WO 2012/151525, and WO 2013/164801, all of which are hereby incorporated by reference.

Pharmaceutical Compositions

The invention provides a pharmaceutical composition comprising one or more compounds of the present invention and one or more pharmaceutically acceptable carriers or excipients. In one embodiment, the pharmaceutical composition includes a therapeutically effective amount of a compound of the present invention. The pharmaceutical composition may include one or more additional active ingredients as described herein.

The pharmaceutical carriers and/or excipients may be selected from diluents, fillers, salts, disintegrants, binders, lubricants, glidants, wetting agents, controlled release matrices, colorants, flavorings, buffers, stabilizers, solubilizers, and combinations thereof.

In one embodiment, the pharmaceutical compositions described herein contain from about 0.1 mg to about 1,000 mg, such as from about 1 mg to about 1,000 mg or from about 20 mg to about 800 mg or 50 mg to about 600 mg or 50 mg to about 600 mg of one or more compounds of the present invention. 100 mg to about 400 mg of one or more compounds of the present invention.

The pharmaceutical compositions of the present invention can be administered alone or in combination with one or more other active agents. Where desired, the subject compounds and other agent(s) may be mixed into a preparation or both components may be formulated into separate preparations to use them in combination separately or at the same time.

The compounds and pharmaceutical compositions of the present invention can be administered by any route that enables delivery of the compounds to the site of action, such as orally, intranasally, topically (e.g., transdermally), intraduodenally, parenterally (including intravenously, intraarterially, intramuscularly, intravascularly, intraperitoneally or by injection or infusion), intradermally, by intramammary, intrathecally, intraocularly, retrobulbarly, intrapulmonary (e.g., aerosolized drugs) or subcutaneously (including depot administration for long term release e.g., embedded-under the-splenic capsule, brain, or in the cornea), sublingually, anally, rectally, vaginally, or by surgical implantation (e.g., embedded under the splenic capsule, brain, or in the cornea).

The compositions can be administered in solid, semi-solid, liquid or gaseous form, or may be in dried powder, such as lyophilized form. The pharmaceutical compositions can be packaged in forms convenient for delivery, including, for example, solid dosage forms such as capsules, sachets, cachets, gelatins, papers, tablets, suppositories, pellets, pills, troches, and lozenges. The type of packaging will generally depend on the desired route of administration. Implantable sustained release formulations are also contemplated, as are transdermal formulations.

Methods of Treatment

The amount of the compound to be administered is dependent on the mammal being treated, the severity of the disorder or condition, the rate of administration, the disposition of the compound and the discretion of the prescribing physician. However, an effective dosage is in the range of about 0.001 to about 100 mg/kg body weight per day, preferably about 1 to about 35 mg/kg/day, in single or divided doses. For a 70 kg human, this would amount to about 0.05 to 7 g/day, preferably about 0.05 to about 2.5 g/day An effective amount of a compound of the invention may be administered in either single or multiple doses (e.g., twice or three times a day).

The compounds of the present invention may be used in combination with one or more of anti-cancer agents (e.g., chemotherapeutic agents), therapeutic antibodies, and radiation treatment.

The compounds of the invention may be formulated or administered in conjunction with other agents that act to relieve the symptoms of inflammatory conditions such as encephalomyelitis, asthma, and the other diseases described herein. These agents include non-steroidal anti-inflammatory drugs (NSAIDs).

EXAMPLES

The examples and preparations provided below further illustrate and exemplify the compounds of the present invention and methods of preparing such compounds. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

As used herein, superscript 1 refers to International Publication No. WO 11/055,215 and superscript 2 refers to International Publication No. WO 12/151,525. These references describe how various intermediates are prepared.

INTERMEDIATES

Intermediate 1: 3-(3-fluorophenyl)-2-(1-hydroxypropyl)-4H-chromen-4-one

To a solution of 2-(1-bromopropyl)-3-(3-fluorophenyl)-4H-chromen-4-one[1] (8.80 g, 24.36 mmol) in DMSO (85 ml), n-butanol (5 ml) was added and heated to 120° C. for 3 h. The reaction mixture was cooled to room temperature (RT), quenched with water and extracted with ethyl acetate. The organic layer was dried over sodium sulphate and concentrated under reduced pressure. The crude product was purified by column chromatography with ethyl acetate:petroleum ether to afford the title compound as a yellow solid (2.10 g, 29%) which was used without further purification in next step.

Intermediate 2: 3-(3-fluorophenyl)-2-propionyl-4H-chromen-4-one

DMSO (1.90 ml, 26.82 mmol) was added to dichloromethane (70 ml) and cooled to −78° C. Oxalyl chloride (1.14 ml, 13.41 mmol) was then added. After 10 minutes, intermediate 1 (2.00 g, 6.70 mmol) in dichloromethane (20 ml) was added dropwise and stirred for 20 min. Triethylamine (7 ml) was added and stirred for 1 h. The reaction mixture was quenched with water and extracted with dichloromethane. The organic layer was dried over sodium sulphate and concentrated under reduced pressure. The crude product was purified by column chromatography with ethyl acetate:petroleum ether to afford the title compound as a yellow liquid (1.20 g, 60%) which was used as such in next step.

Intermediate 3: (+)/(−)-3-(3-fluorophenyl)-2-(1-hydroxypropyl)-4H-chromen-4-one To a solution of intermediate 2 (0.600 g, 2.02 mmol) in DMF (7.65 ml) under nitrogen purging, formic acid:trietylamine 5:2 azeotrope (1.80 ml) was added followed by [(S,S)tethTsDpenRuCl] (3.0 mg). The reaction mixture was heated at 80° C. for 1.5 hours under continuous nitrogen purging. The reaction mixture was quenched with water, extracted with ethyl acetate, dried over sodium sulphate and concentrated. The crude product was purified by column chromatography with ethyl acetate:petroleum ether to afford the title compound as a yellow solid (0.450 g, 74%). Mass: 299.0 (M+). Enantiomeric excess: 78%, enriched in the late eluting isomer (retention time: 9.72 min.) as determined by HPLC on a chiralpak AD-H column.

Intermediate 4: (+)/(−)-3-(3-fluorophenyl)-2-(1-hydroxypropyl)-4H-chromen-4-one The title compound was obtained as yellow solid (0.500 g, 83%) by using a procedure similar to the one described for intermediate 3, using intermediate 2 (0.600 g, 2.02 mmol), DMF (7.65 ml), formic acid:trietylamine 5:2 azeotrope (1.80 ml) and [(R,R)tethTsDpenRuCl] (3.0 mg). Mass: 298.9 (M+). Enantiomeric excess: 74.8%, enriched in the fast eluting isomer (retention time: 8.52 min.) as determined by HPLC on a chiralpak AD-H column.

Intermediate 5: (R)-3-(3-fluorophenyl)-2-(1-hydroxypropyl)-4H-chromen-4-one

Step 1: (R)-2-(1-(benzyloxy)propyl)-3-(3-fluorophenyl)-4H-chromen-4-one: To 2-(3-fluorophenyl)-1-(2-hydroxyphenyl)ethanone (2.15 g, 9.36 mmol), in dichloromethane (20 ml), HATU (4.27 g, 11.23 mmol), R-(+)2-benzyloxybutyric acid (2.00 g, 10.29 mmol) were added and stirred for 10 min, then triethylamine (14.0 ml, 101.1 mmol) was added dropwise and stirred at RT for 24 h. The reaction mixture was quenched with water, extracted with dichloromethane, dried over sodium sulphate and concentrated under reduced pressure. The crude product was purified by column chromatography with ethyl acetate:petroleum ether to afford the title compound as yellow solid (1.65 g, 45%). $^1$H-NMR (δ ppm, CDCl$_3$, 400 MHz): 8.24 (dd, J=7.9, 1.5 Hz, 1H), 7.74 (dt, J=7.1, 1.7 Hz, 1H), 7.58 (dd, J=8.3, 0.4 Hz, 1H), 7.44-7.06 (m, 10H), 4.51 (d, J=7.8 Hz, 1H), 4.34 (d, J=7.8 Hz, 1H), 4.25 (dd, J=7.8, 6.2 Hz, 1H), 2.17-1.90 (m, 2H), 0.95 (t, J=7.5 Hz, 3H). Mass: 389.0 (M+).

Step 2: (R)-3-(3-fluorophenyl)-2-(1-hydroxypropyl)-4H-chromen-4-one: To (R)-2-(1-(benzyloxy)propyl)-3-(3-fluorophenyl)-4H-chromen-4-one (1.50 g, 3.86 mmol) in dichloromethane (15 ml) cooled to 0° C. and aluminium chloride (1.00 g, 7.72 mmol) was added portion wise and stirred at RT for 6 h. The reaction mixture was quenched with 2N HCl solution, extracted with dichloromethane, dried over sodium sulphate and concentrated under reduced pressure. The crude product was purified by column chromatography with ethyl acetate:petroleum ether to afford the title compound as yellow solid (0.552 g, 48%). $^1$H-NMR (δ ppm, CDCl$_3$, 400 MHz): 8.24 (dd, J=8.0, 1.6 Hz, 1H), 7.72 (m, 1H), 7.52 (dd, J=8.4, 0.5 Hz, 1H), 7.44 (m, 2H), 7.12-7.01 (m, 3H), 4.49 (t, J=7.0 Hz, 1H), 1.94 (m, 2H), 0.93 (t, J=7.5 Hz, 3H). Mass: (299.0 (M+). Purity: 96.93%. $[\alpha]^{25}_D$ −14.73 (c=1, CHCl$_3$). Enantiomeric excess: 85.92%, enriched in the fast eluting isomer (retention time: 8.57 min.) as determined by HPLC on a chiralpak AS-3R column.

Compound A (RS)-2-(1-(9H-purin-6-ylamino)propyl)-3-(3-fluorophenyl)-4H-chromen-4-one To a solution of intermediate 1 (2.50 g, 8.41 mmol) in THF (25 ml), tert-butyl 9-trityl-9H-purin-6-ylcarbamate (4.81 g, 10.09 mmol) and triphenylphosphine (3.31 g, 12.62 mmol) were added and stirred at RT for 5 min. Diisopropylazodicarboxylate (2.5 ml, 12.62 mmol) was added and stirred at RT for 2 h. The reaction mixture was concentrated and column chromatographed with ethyl acetate:petroleum ether to afford a yellow coloured intermediate. To the intermediate, dichloromethane (65 ml) and trifluoroacetic acid (7.9 ml) were added and the resulting mixture was stirred at RT for 12 h. The reaction mixture was then basified with aqueous sodium bicarbonate solution, extracted with dichloromethane and dried over sodium sulphate. The crude product was purified by column chromatography with methanol:dichloromethane to afford the title compound as pale-brown solid (1.05 g, 30%). MP: 148-150° C. Mass: 415.6 (M+).

Compound A1

(S)-2-(1-(9H-purin-6-ylamino)propyl)-3-(3-fluorophenyl)-4H-chromen-4-one

Method A:
To a solution of intermediate 3 (0.250 g, 0.838 mmol) in THF (5 ml), tert-butyl 9-trityl-9H-purin-6-ylcarbamate (0.479 g, 1.00 mmol) and triphenylphosphine (0.329 g, 1.25 mmol) were added and the resulting mixture was stirred at RT for 5 min. Diisopropylazodicarboxylate (0.25 ml, 1.25 mmol) was then added and stirred at RT for 12 h. The reaction mixture was concentrated and column chromatographed with ethyl acetate:pet. ether to afford the yellow coloured intermediate. To the intermediate in dichloromethane (6 ml), trifluoroacetic acid (1.2 ml) was added stirred at RT for 12 h. The reaction mixture was basified with aqueous sodium bicarbonate solution, extracted with dichloromethane and dried over sodium sulphate. The crude product was purified by column chromatography with methanol:dichloromethane to afford the title compound as an off-white solid (0.015 g, 4%). MP: 137-140° C. $^1$H-NMR (δ ppm, DMSO-$d_6$, 400 MHz): 12.94 (s, 1H), 8.12-8.10 (m, 4H), 7.84-7.80 (m, 1H), 7.61 (d, J=8.3 Hz, 1H), 7.50-7.41 (m, 2H), 7.28-7.18 (m, 3H), 5.20-5.06 (m, 1H), 2.10-1.90 (m, 2H), 0.84 (t, J=3.7 Hz, 3H). Enantiomeric excess: 77.4% as determined by HPLC on a chiralpak AD-H column, enriched in the fast eluting isomer (retention time=7.90 min.).

Method B:

To a solution of intermediate 5 (2.60 g, 8.68 mmol) in THF (52 ml), tert-butyl 9-trityl-9H-purin-6-ylcarbamate (4.96 g, 10.42 mmol) and triphenylphosphine (2.76 g, 13.03 mmol) were added and the resulting mixture was stirred at RT for 5 min. Diisopropylazodicarboxylate (0.25 ml, 1.25 mmol) was then added and stirred at RT for 12 h. The reaction mixture was concentrated and column chromatographed with ethyl acetate:petroleum ether to afford the yellow coloured intermediate. To the intermediate in dichloromethane (55 ml), trifluoroacetic acid (14.2 ml) was added and stirred at RT for 12 h. The reaction mixture was basified with aqueous sodium bicarbonate solution, extracted with dichloromethane and dried over sodium sulphate. The crude product was purified by column chromatography with methanol:dichloromethane to afford the title compound as pale-yellow solid (1.00 g, 27%). MP: 168-170° C. Mass: 416.5 ($M^+$+1) Enantiomeric excess: 86.5% as determined by HPLC on a chiralpak AD-H column, enriched in the fast eluting isomer (retention time=7.90 min.).

Method C:

The title compound was separated by preparative SFC conditions from Compound A (1.090 g) on a CHIRALPAK AY-H column (250×30 mm; 5 μm) using methanol:$CO_2$ (35:65) as the mobile phase at a flow rate of 80 g/min. Off-white solid (0.378 g). e.e. 100%. Rt: 2.37 min. Mass: 416.1 ($M^+$+1). MP: 149-152° C.

Compound A2

(R)-2-(1-(9H-purin-6-ylamino)propyl)-3-(3-fluorophenyl)-4H-chromen-4-one

Method A:

The title compound was obtained as an off-white solid (0.015 g, 4%) by using a procedure similar to the one described for compound A1 (Method A) using tert-butyl 9-trityl-9H-purin-6-ylcarbamate (0.479 g, 1.00 mmol), intermediate 4 (0.250 g, 0.838 mmol), triphenylphosphine (0.329 g, 1.25 mmol), THF (5 ml) and diisopropylazodicarboxylate (0.25 ml, 1.25 mmol), followed by the cleavage of the intermediate with trifluoroacetic acid (1.2 ml) and dichloromethane (6 ml). MP: 139-141° C. Mass: 415.6 (M+). Enantiomeric excess: 81.6% as determined by HPLC on a chiralpak AD-H column, enriched in the late eluting isomer (retention time=10.81 min.).

Method B:

The title compound was separated by preparative SFC conditions from Compound A (1.090 g) on a CHIRALPAK AY-H column (250×30 mm; 5 μm) using methanol:$CO_2$ (35:65) as the mobile phase at a flow rate of 80 g/min. Off-white solid (0.434 g). e.e. 98%. Rt: 3.71 min. Mass: 416.1 ($M^+$+1). MP: 162-164° C.

BIOLOGICAL ASSAYS

The pharmacological properties of the compounds described herein may be confirmed by a number of pharmacological assays. The pharmacological assays which have been carried out with the compounds according to the invention and/or their pharmaceutically acceptable salts are exemplified below Assay 1: Fluorescent Determination of PI3 Kinase Enzyme Activity Phosphoinositide 3 kinases (PI3K) belong to a class of lipid kinases that play a critical role in the regulation of several key cellular processes. The PI3K are capable of phosphorylating the 3-hydroxy position of phosphoinositols thereby generating second messengers involved in downstream signalling events. The homogenous time resolved fluorescence (HTRF) assay allows detection of 3,4,5-triphosphate (PIP3) formed as a result of phosphorylation of phosphotidylinositol 4,5-biphosphate (PIP2) by PI3K isoforms such as α, β, γ or δ.

PI3K isoform activity for α, β, γ or δ was determined using a PI3K human HTRF™ Assay Kit (Millipore, Billerica, Mass.) with modifications. All incubations were carried out at room temperature. Briefly, 0.5 μl of 40× inhibitor (in 100% DMSO) or 100% DMSO were added to each well of a 384-well white plate (Greiner Bio-One, Monroe, N.C.) containing 14.5 μl 1× reaction buffer/PIP2 (10 mM $MgCl_2$, 5 mM DTT, 1.38 μM PIP2) mix with or without enzyme, followed by 5 μl/well of 400 μM ATP and incubated for an additional 30 minutes. Reaction was terminated by adding 5 μl/well stop solution (Millipore, Billerica, Mass.). 5 μl of detection mix (Millipore, Billerica, Mass.) were then added to each well and was incubated for 6-18 hours in the dark. HRTF ratio was measured on a microplate reader (BMG Labtech., Germany) at an excitation wavelength of 337 nm and emission wavelengths of 665 and 615 nm with an integration time of 400 msec counting delay of 50 msec. The results for Compounds A1 and A2 are shown in Table 1 below. Comparative data for Compound A1 and Example 47 of WO 11/055,215 are provided in Table 2.

TABLE 1

| Compound | $IC_{50}$ (nM) | | | |
|---|---|---|---|---|
| | Pi3Kδ | Pi3Kα | Pi3Kβ | Pi3Kγ |
| A1 | 23.85 | >10000 | >4000 | 24.05 |
| A2 | >10 μM | ND | ND | >10 μM |

TABLE 2

| Compound | PI3Kδ | PI3Kγ | |
|---|---|---|---|
| | $IC_{50}$ in nM | % Inhibition at 1 μm | $IC_{50}$ in nM |
| Example 47 of WO 11/055215 | 105.9 | 25.54 | ND |
| Compound A1 | 23.85 | — | 24.05 |

Assay 2: In Vitro Cell Proliferation Assay in Leukemic Cell Lines

Growth inhibition assays were carried out using 10% FBS supplemented media. Cells were seeded at a concentration of 5000-20,000 cells/well in a 96-well plate. Test compounds at a concentration range from 0.01 to 10000 nM were added after 24 h. Growth was assessed using the 3-[4,5-dimethyl-thiazol-2-yl]-2,5-diphenyltetrazolium bromide (MTT) dye reduction test at 0 h (prior to the addition of the test compound) and 72 h after the addition of test compound. Absorbance was read on a Fluostar Optima (BMG Labtech, Germany) at a wave length of 450 nm. Data were analysed using GraphPad Prism and percent inhibition due to the test compound compared to the control was calculated accordingly.

Compound A1 caused a reduction in T-lymphoma (MOLT-4, Jurkat, CCRF-CEM, Hut-78 & HuT-102) cell viability with $GI_{50}$ values ranging from 1-5 µM for the dose range tested. Additionally, the compound did not display any apparent cytotoxicity over the 72-h incubation period up to 10 µM.

Assay 3: Inhibition of AKT Phosphorylation in Leukemic Cell Lines

MOLT-4, Jurkat, CCRF-CEM, Hut-78, HuT-102, Sez4 and HH cells were incubated with desired concentrations of compound for 48 h. Cells were lysed and pAKT determined by Western Blotting. Bands were quantified using ImageJ and normalized to actin.

Figure 8:
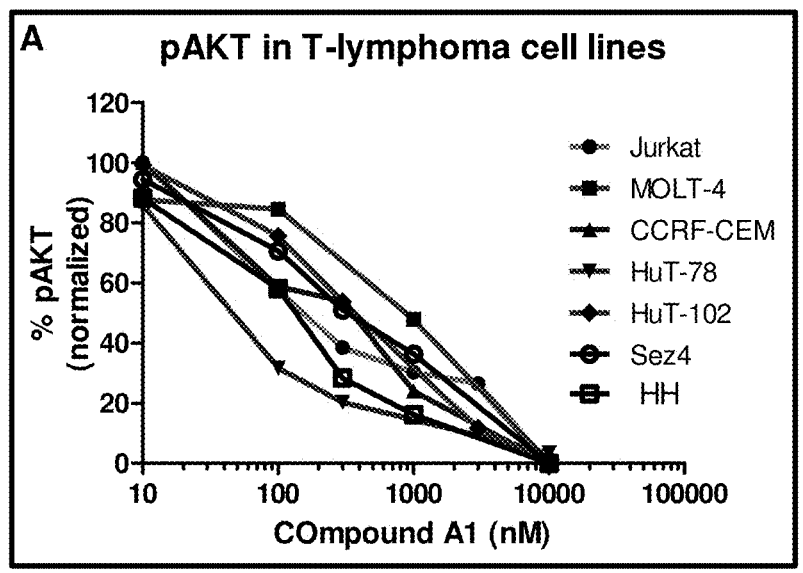
FIG. 8 depicts a graph showing the inhibition of AKT phosphorylation in leukemic cell lines (MOLT-4, Jurkat, CCRF-CEM, Hut-78, and HuT-102) by Compound A1 according to the procedure in Assay 3.

Compound A1 caused a reduction in pAKT expression in T-lymphoma (MOLT-4, Jurkat, CCRF-CEM, Hut-78 & HuT-102) cell lines with EC50 values ranging from 0.5-2 µM for the dose range tested. The results are shown in FIG. 8.

Assay 4: Inhibition of PI3K δ and γ Signalling in Basophils from Human Whole Blood PI3K δ and γ signalling in basophils manifested by an alteration of anti-FcεR1 or fMLP induced CD63 expression is a useful pharmacodynamic marker determined using the Flow2CAST® kit (Buhlmann Laboratories, Switzerland). Briefly, it involves the following steps:

Mix the anti-coagulated blood sample by inverting the venipuncture tube several times;
Prepare fresh and pyrogen-free 3.5 ml polypropylene or polystyrene tubes suitable for Flow Cytometry measurements;
Add 49 µl of patient's whole blood to each tube;
Add 1 µl of 10% DMSO (background) or compound (10% DMSO) to the assigned tubes and mix gently. Incubate at room temperature for 15 minutes;
Pipet 50 µl of the Stimulation buffer (background) or anti-FcεRI Ab or fMLP to each tube;
Add 100 µl of Stimulation Buffer to each tube;
Mix gently. Add 20 µl Staining Reagent (1:1 mix of FITC-CD63 and PE-CCR3) to each tube;
Mix gently, cover the tubes and incubate for 15 minutes at 37° C. in a water bath. (using an incubator will take about 10 minutes longer incubation time due to less efficient heat transfer);
Add 2 ml pre-warmed (18-28° C.) Lysing Reagent to each tube, mix gently;
Incubate for 5-10 minutes at 18-28° C.;
Centrifuge the tubes for 5 minutes at 500×g;
Decant the supernatant by using blotting paper;
Resuspend the cell pellet with 300-800 µl of Wash Buffer; and
Vortex gently and acquire the data on the flow cytometer within the same day.

Percent CD63 positive cells within the gated basophil population were determined in different treatment groups and normalized to vehicle control.

Figure 9:
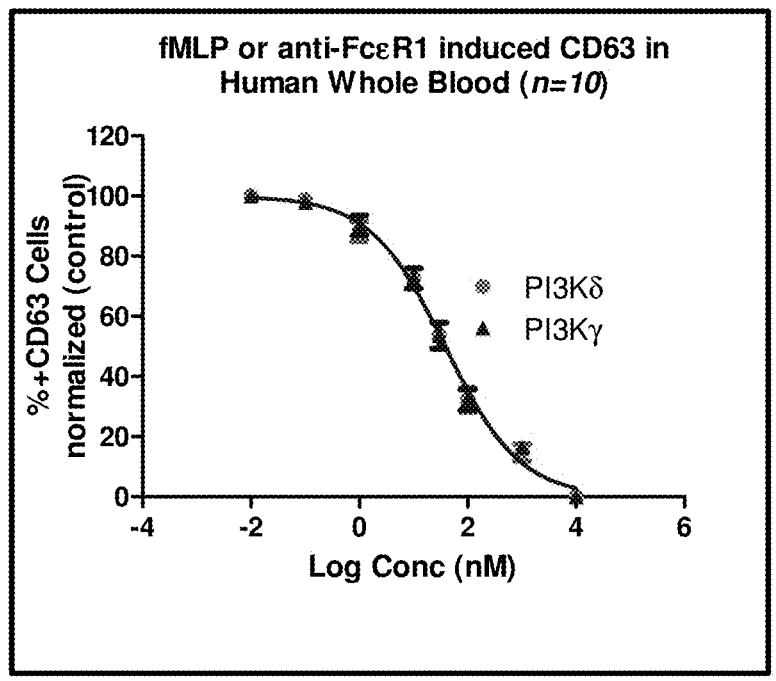
FIG. 9 depicts a graph showing the inhibition in percentage of CD63 positive cells induced by fMLP or anti-FcεR1 in human whole blood by Compound A1 according to the procedure in Assay 4.

Compound A1 exhibited a $EC_{50}$ of <40 nM for FcεR1 (PI3K δ) and a $IC_{50}$ of <40 nM for fMLP (PI3K γ) (n=10). The results are shown in FIG. 9.

Assay 4a: Cellular Activity Demonstrating Selectivity of Compound A1 Towards PI3K Delta and PI3K Gamma Isoform Assay 4A1: Anti-IgM Induced B-Cell Proliferation (for PI3Kδ Selectivity)

The objective of this study was to assess the inhibitory potential of Compound A1 on anti-IgM induced human B-cell proliferation.

Plating and Treatment

Isolated B-cells were re-suspended to $1.0 \times 10^6$ cells per ml. 100 µl of cell suspension was added to each well of a 96-well plate. Triplicates were maintained.
50 µl of drug dilution was added and mixed well. A DMSO blank and inducer blank were maintained.
Treated plate was incubated for 30 min at 37° C., 5% $CO_2$ and then 50 µl of 4× inducer was added and mixed by pipetting.
Plate was incubated at 37° C., 5% $CO_2$ for 72 h.
Media was aspirated and 150 µl of DMSO was added to dissolve the formazan crystals.
Absorbance was read at $A_{560}$ and $A_{640}$ nm.

The data demonstrates the inhibitory potential of Compound A1 on PI3Kδ mediated induction of human B-cell proliferation. See, e.g., Baeker et al. *Journal of Immunology*, 134: 3532-3538, 1985.

Assay 4A2: LPA Induced AktS473 Phosphorylation in 3T3 Fibroblasts (for PI3Kβ Selectivity)

The objective of this study was to determine the effect of Compound A1 on PI3Kβ kinase mediated LPA induced AktS473 phosphorylation in 3T3 fibroblasts.

3T3 cells were treated with desired concentrations of the test compound for 15 min. 1 ml of 2×LPA was added such that the final concentration was 5 µM and incubated for 5 min.
Media was discarded and washed with 1 ml of ice-cold 1×PBS.
250 µl of cell lysis buffer was added and incubated on ice for 30 min.
Samples were centrifuged and supernatant was at −80° C. until analysis.
Samples were analyzed by Western Blotting using pAKT (S473) as the primary and anti-rabbit IgG-HRP as a secondary antibody.
Intensity of the bands was determined using ImageJ 1.42q (NIH, USA) and normalized to Actin (loading control).
Data was plotted using GraphPad Prism (Version 5.02).

The results demonstrate the selectivity of Compound A1 over the beta isoform of PI3K. See Albuquerque et al., *J. Biol. Chem.* 278, 39830-39838, 2003.

Assay 4A3: c5a Induced AktS473 Phosphorylation in RAW 264.7 Macrophages (for PI3Kγ Selectivity)

The objective of this study was to determine the effect of Compound A1 on PI3Kγ kinase mediated c5a induced AktS473 phosphorylation in RAW 264.7 macrophages.

RAW 264.7 cells were treated with desired concentrations of the test compound for 15 min. 1 ml of 2×c5a was added such that the final concentration was 50 ng/ml and incubated for 15 min.
Media was discarded and washed with 1 ml of ice-cold 1×PBS.

250 µl of cell lysis buffer was added and incubated on ice for 30 min.

Samples were centrifuged and supernatant was stored at −80° C. until analysis

Samples were analyzed by Western Blotting using pAKT (S473) as the primary and anti-rabbit IgG-HRP as a secondary antibody.

Intensity of the bands was determined using ImageJ 1.42q (NIH, USA) and normalized to Actin (loading control). Data was plotted using GraphPad Prism (Version 5.02).

Inhibition of pAktS473, a downstream marker of PI3Kδ signaling suggests a role for Compound A1 in the oncogenic pathways regulated by Akt in c5a induced RAW 264.7 cells. See To et al. *Am. J. Respir. Crit. Care Med.*, 182, 897-904, 2010.

Assay 4A4: PDGF Induced Akt Phosphorylation in 3T3 Cells (for PI3K α Selectivity)

The objective of this study was to determine the effect of Compound A1 on PI3Kα kinase mediated AktS473 phosphorylation in PDGF induced 3T3 fibroblasts.

3T3 cells were treated with desired concentrations of the test compound for 15 min. 1 ml of 2×PDGF was added such that the final concentration was 20 ng/ml and incubated for 10 min.

Media was discarded and washed with 1 ml of ice-cold 1×PBS.

250 µl of cell lysis buffer was added and incubated on ice for 30 min.

Samples were centrifuged and supernatant was collected and stored at −80° C. until analysis.

Samples were analyzed by Western Blotting using pAKT (S473) as the primary and anti-rabbit IgG-HRP as a secondary antibody.

Intensity of the bands was determined using ImageJ 1.42q (NIH, USA) and normalized to Actin (loading control). Data was plotted using GraphPad Prism (Version 5.02).

No inhibition was observed at 10 µM of Compound A1, demonstrating the selectivity of Compound A1 over the alpha isoform of PI3K. See Albuquerque et al., *J. Biol. Chem.* 278, 39830-39838, 2003.

The Table below summarizes the results from Assays 4A1-4A4.

| CELLULAR ACTIVITY DEMONSTRATING SELECTIVITY OF COMPOUND A1 TOWARDS PI3K DELTA AND PI3K GAMMA ISOFORM | |
| --- | --- |
| Cellular IC$_{50}$ PI3K alpha (PDGF induced pAKT in 3T3 fibroblasts) | >10000 nM |
| Cellular IC$_{50}$ PI3K beta (LPA induced pAKT in 3T3 fibroblasts) | 2067 nM |
| Cellular IC$_{50}$ PI3K delta (anti-IgM induced human B-cell proliferation) | 38.1 nM |
| Cellular IC$_{50}$ PI3K gamma (c5a induced pAKT in RAW macrophages) | 22.3 nM |

Assay 5: Inhibition of Apoptosis in Leukemic Cell Lines

Apoptosis in leukemic cells was determined using an in-situ Caspase 3 kit (Millipore, US) as outlined below:

Seed leukemic cells—at a density of 1×10$^6$ cells/well in a 6 well plate

Add test compound/DMSO at desired concentrations

Incubate the plate for 24 hrs at 37° C. in 5% $CO_2$ incubator

Collect cells in a 2 ml centrifuge tube

Add 1.6 µL of freshly prepared 5×FLICA reagent and mix cells by slightly flicking the tubes Incubate tubes for 1 hour at 37° C. under 5% $CO_2$ Add 2 ml of 1× wash buffer to each tube and mix Centrifuge cells at <400×g for 5 minutes at room temperature.

Carefully remove and discard supernatant, and gently vortex cell pellet to disrupt any cell-to-cell clumping.

Resuspend cell pellet in 300 ul of 1× wash buffer

Place 100 µL of each cell suspension into each of two wells of a black microtiter plate. Avoid creation of bubbles.

Read absorbance of each microwell using an excitation wavelength of 490 nm and an emission wavelength of 520 nm Percent increase in caspase-3 activity manifested by an increase in fluorescence compared to the control blank is to be calculated.

Compound A1 caused a dose-dependent induction in caspase-3 activity in T-lymphoma (MOLT-4, Jurkat, CCRF-CEM, Hut-78 & HuT-102) cell lines.

Assay 6: Screening for pAKT Inhibition in Human Primary CTCL Cells

Flow cytometry analysis of pAKT inhibition: Purified malignant T cells were isolated from donors and cultured overnight in RPMI/1% BSA. Cells were incubated with the test compound for 1.5 hr with a cytokine mix added for the final 30 minutes. The composition of the cytokine mix was 20 ng/ml IL2+5 ng/ml IL7+10 ng/ml IL15+10% FBS. AKT phosphorylation was determined by flow cytometry.

Treatment with Compound A1 caused a dose dependent reduction AKT phosphorylation with EC$_{50}$ ranging from 40-300 nM (% inhibition data).

Assay 6A: Screening for Anti-Cancer Activity in Human CLL Cells

Primary CLL cells were enriched using Rosette-Sep B cells from Stem Cell Technology, generally giving purity of >97% of B cells/CLL cells. Cells were seeded at 2.5×10$^5$ per well in a 96 well with either serum free medium (SFM) or SFM+10% heat-inactivated fetal bovine serum (volume 100 microliters) in the presence of desired concentrations of the test compound and cultured for 3 days at 37° C. in a carbon dioxide incubator. Cytotoxicity was determined using the MTS assay.

Compound A1 induces cytotoxicity in CLL cells with a median EC$_{50}$ of <100 nM in serum-free and <700 nM in 10% FBS media.

Assay 6B: Screening for Anticancer Activity in Patient Derived B-Lymphoma Cells

Primary cells from lymphoid tumors were exposed to the test compound [Compound A1] to assess the induction of cell death. Cells were derived from diffuse large B-cell lymphoma (DLBCL), mantle cell lymphoma (MCL), splenic marginal zone lymphoma (SMZL), extranodal marginal zone lymphoma (EMZL), or chronic lymphocytic leukemia (CLL, no.=1). Cells were treated with desired concentrations of the compound and apoptosis (Annexin V/PI) was assessed by flow-cytometry after a 48-h incubation period.

Almost all the primary cells derived from B-cell lymphomas underwent an increase in cell death when exposed to the test compound (Compound A1) at a concentration of 4 µM. The phenomenon appeared more evident among primary cells derived from small cell lymphomas (MZL, MCL, and CLL).

Assay 6C: Inhibition of AKT Phosphorylation in B-Lymphoma Cell Lines

LY-1, LY-10, Daudi, JEKO, REC and MAVER cells were incubated with desired concentrations of [compound A1] for 48 hours. Cells were lysed and pAKT was determined by Western Blotting. Bands were quantified using ImageJ and normalized to actin.

Compound A1 exhibited an $EC_{50}$ of 20-200 nM across the B-lymphoma cell lines tested.

Assay 6D: Cytokine Assay in Anti-Human CD3 and CD28 Vo-Stimulated Primary T-Cells The objective of this study was to assess the inhibitory potential of Compound A1 on cytokines produced by anti-human CD3/CD28 co-stimulated primary T-cells.

Plating and Treatment

Plates were coated with 50 µl of anti-human CD3 at a concentration of 100 ng/ml either overnight at 4° C. or for 2 h at 37° C. After incubation, plates were washed twice with sterile PBS to remove unbound antibody.

Isolated human T-cells were re-suspended to $0.625 \times 10^6$ cells per ml in 1.5 ml tubes and 1 µl of drug dilution (1000×) was added. A DMSO blank and un-induced blank were maintained.

Cells were incubated with compound at room temperature for 30 min and then added to anti-human CD3 coated wells of a 96-well plate, 240 µl each. Anti-human CD28 was added immediately, 10 µl (25×) per well.

Plate was incubated at 37° C., 5% $CO_2$ for 24 h.

Plates were centrifuged at 4000 rpm at room temperature, supernatant was collected and stored at −20° C.

Cytokines were determined using a commercial ELISA kit with absorbance read at 450 and 570 nm.

Figure 10:
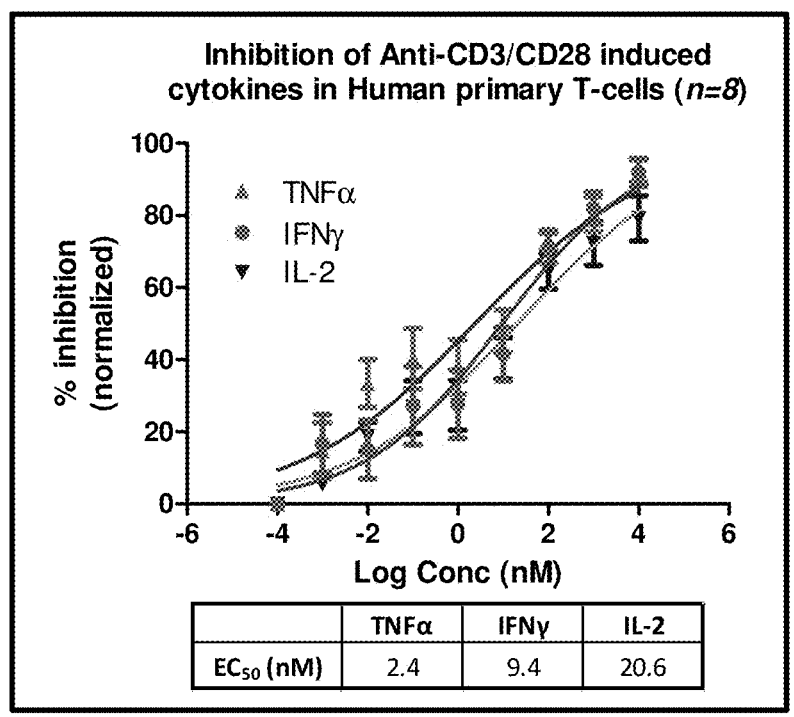
FIG. 10 depicts a graph showing the inhibition of anti-human CD3/CD28-induced cytokines (TNFα, IFNγ and IL2) by Compound A1 according to Assay 6D.

$IC_{50}$ values were calculated from eight independent experiments. Compound A1 inhibited anti-human CD3-CD28 induced T cell cytokines with an $IC_{50}$ of 24, 9.54 and 20.6 nM for TNFα, IFNγ and IL2 respectively. The results are shown in FIG. 10.

Assay 7: Lipopolysaccharide Induced Pulmonary Neutrophilia in Female Wistar Rat Model An exaggerated recruitment and subsequent activation of neutrophil is likely to be important for the development and course of several inflammatory diseases in the airways and lungs, such as severe asthma, chronic obstructive pulmonary disease, cystic fibrosis, and acute respiratory distress syndrome. The mechanisms by which neutrophil contribute to these diseases may involve the release of proteolytic enzymes, such as neutrophil elastase, and free oxygen radicals. When released, these compounds can cause bronchoconstriction, bronchial hyperreactivity, hyper-secretion, epithelial damage, and tissue remodelling in the airways.

After the quarantine period, fasted animals were randomized and divided into various groups depending on their body weights. The test compound [Compound A1] was prepared as a suspension in a vehicle consisting of 0.5% methylcellulose in which Tween 80 as a suspending agent. The compound or vehicle was administered by oral gavage in a volume of 10 mL/kg. Female Wistar rats were anaesthetized with ketamine and LPS solution was administered intratracheally one hour after compound administration at a dose of 1 mg/kg. 6 h after LPS instillation, animals were exsanguinated under anaesthesia, and then trachea was cannulated and the lungs were lavaged with 5-ml aliquots of heparinised PBS (1 unit/ml) four times through tracheal cannula (total volume 20 ml). Bronchioalveolar lavage (BAL) fluid was been stored at 2-8° C. until assayed for total cell and differential leukocyte count. Bronchioalveolar fluid was centrifuged (500×g for 10 min) and the resulting cell pellet was resuspended in 0.5 ml of heparinised saline. The total numbers of white blood cells were determined in BAL fluid or blood by using a blood cell counter and was adjusted to $1 \times 10^6$ cell/ml. Differential cell count was calculated manually. One hundred microliters of the cell suspension was centrifuged using cytospin 3 to prepare a cell smear. The cell smear was stained with a blood staining solution for differentiation and slides were microscopically observed to identify eosinophil according to their morphological characteristics. The number of each cell type among 300 white blood cells in the cell smear was determined and expressed as a percentage. The number of eosinophil in each BALf or blood was calculated.

Compound A1 showed a dose-dependent reduction of neutrophil infiltration into the lungs with an $ED_{50}$ of 6.5 mg/kg suggesting a therapeutic role in inflammatory disorders. The results are shown in FIG. 1.

Assay 8: Lipopolysaccharide-Induced Rat Air Pouch Model of Inflammation

Leukocyte recruitment and the formation of pro-inflammatory mediators, including different cytokines, are the hallmark of an inflammatory response. The air-pouch model was originally developed as a facsimile synovium for the study of inflammatory processes that occur in rheumatoid arthritis (RA). The model allows the differential quantification of leukocyte species that accumulate in the air-pouch wall (tissue) as well as those that transmigrate into the air-pouch cavity (lavage), and it allows the characterization of the chemokines and adhesion molecules responsible for diapedesis induced by a variety of inflammatory stimuli.

Female Wistar rats (175-200 g) were acclimatized for seven days prior to the start of the experiment Animals were randomly distributed to various groups based on their body weights Animals were anaesthetised with ether and subcutaneous air pouches were made by injecting 20 ml of sterile air under the skin in the intra-scapular area (day 0) and maintained with a second 10-ml injection of sterile-filtered air on day 4. On day 6, oral treatment was commenced 1 h prior to induction of inflammation by s.c. injection of LPS solution on day 6. A volume of 5-ml of LPS solution dissolved in sterile saline (100 µg/kg) was injected into each pouch. Samples of pouch fluid were taken at 6 h after administration of LPS by flushing the pouch with 5 ml of sterile saline and withdrawing 4 ml of fluid. The numbers of leukocytes present in pouch fluid was determined microscopically using a haemocytometer. Differential cell content was determined by microscopic examination of fluid smears stained with Diff-Quik.

Figure 2:
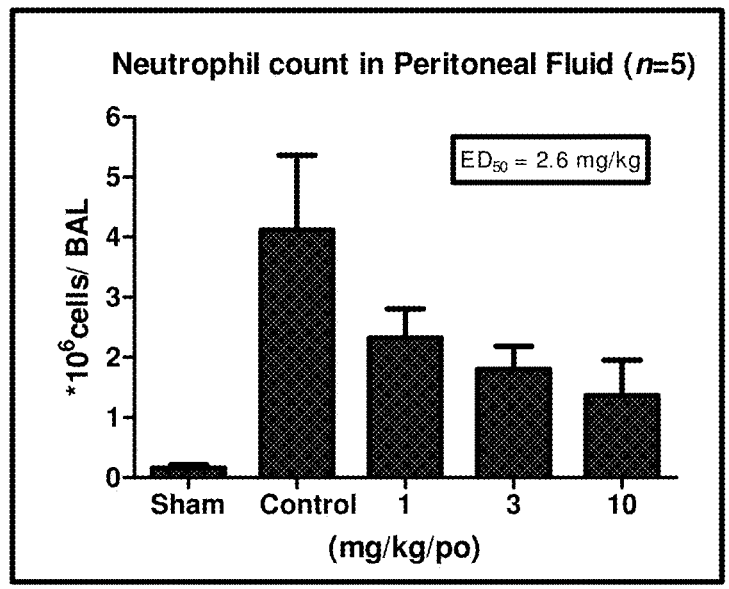
FIG. 2 depicts a bar graph of the neutrophil count in peritoneal lavage fluid from animals treated with 0, 1, 3, and 10 mg/kg of Compound A1 (po) according to the Lipopolysaccharide-induced rat air pouch inflammation model described in Assay 8.

Compound A1 caused a dose-dependent reduction of neutrophil migration into the rat air pouch with an $ED_{50}$ of 2.6 mg/kg suggesting a therapeutic role in rheumatoid arthritis. The results are shown in FIG. 2.

Assay 9: Lipopolysaccharide Induced TNF-α Production

Fasted female wistar rats were randomized into different groups depending on their body weights. Test compound (Compound A1) was prepared as a suspension in a vehicle consisting of 0.5% methylcellulose. The compound or vehicle was administered by oral gavage in a volume of 10 mL/kg. LPS solution was administered intraperitoneally one hour after compound administration at a dose of 0.3 mg/kg. Blood was collected in serum separator tubes via cardiac puncture ninety minutes after LPS injection. Serum was separated and stored at −20° C. and will be analysed for TNFα by ELISA.

Figure 3:
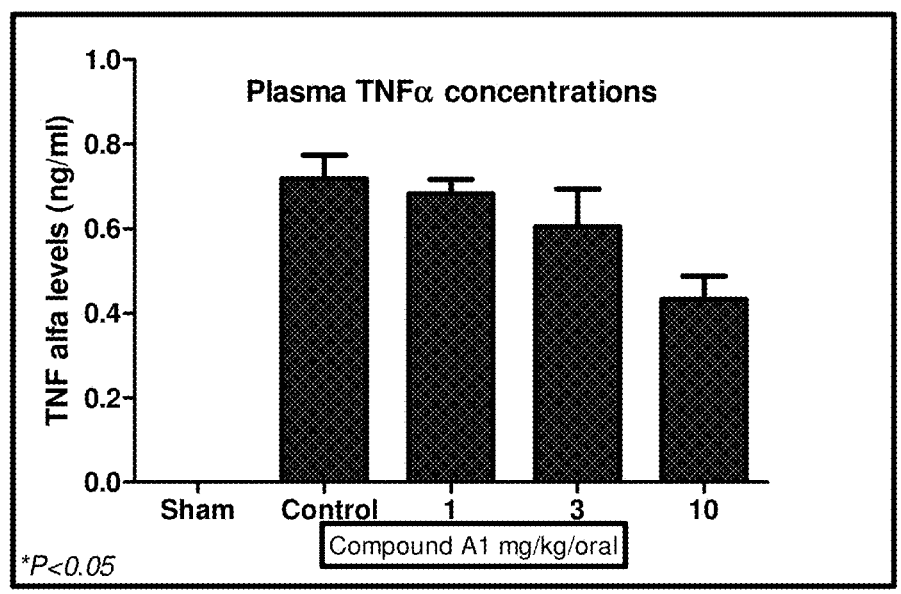
FIG. 3 depicts a bar graph of the Lipopolysaccharide-induced plasma TNF-α concentration in fasted female Wistar rats following administration of 0, 1, 3, and 10 mg/kg of Compound A1 (po) according to the procedure described in Assay 9.

Compound A1 reduced plasma TNFα concentrations suggesting a therapeutic role in inflammatory disorders (percent inhibition observed at 1, 3 and 10 mg/kg was 5%, 15%, and 40%, respectively). The results are shown in FIG. 3.

Assay 10A: Ovalbumin Induced Pulmonary Eosinophilia in Male Guinea Pigs

Airway inflammation and hyper-responsiveness (AHR) are hallmarks and distinguishing features of bronchial asthma. Provocation of pre-sensitized mice with the same allergen induces airway inflammation with preferential eosinophilic infiltration and, as a consequence, AHR. Pulmonary eosinophilia and airway remodelling in conjunction with altered neural control of airway tone and airway epithelial desquamation may contribute to AHR in asthma.

After the quarantine period, 0.3 mL of blood samples was collected from orbital vein by retro-orbital plexus method from each individual animal and analysed on a cell analyser (ADVIA 2120, Siemens). Based on their total cell count, guinea pigs were randomized and divided into various groups. Ear pinna was marked with an indelible marking pen for identification. On day 0, weights were recorded and animals were sensitized with 50 μg of Ovalbumin (OVA) and 10 mg of alum solution (1 mL) intraperitoneally. On day 7 and day 14, the above sensitization protocol was repeated. Animals were observed for any signs of illness or reaction to the sensitization up to day 19 and recorded if any. On day 19, 20, and 21, after the treatment with test compound by oral gavage, 30 mins later animals were exposed to 0.5% w/v, 0.5% and 1% Ovalbumin challenge respectively. Control & sham group animals were treated with 0.5% w/v methyl cellulose (vehicle). Sham control groups were sensitized with 10 mg of alum on day 0, 7 & 14 and exposed to saline solution (SAL) with the same nebulization rate on day 19, 20 and 21. Twenty hours after last OVA challenge, airway hyperresponsiveness was measured by whole body plethysmograph against cumulative doses of methacholine challenge (75, 100, 125 & 150 μg/ml), after measuring the airway response, blood samples and BAL fluid was collected. Samples were analysed for total cell count by using neubuear chamber under microscope and differential leukocyte count was done manually.

Figure 4A:
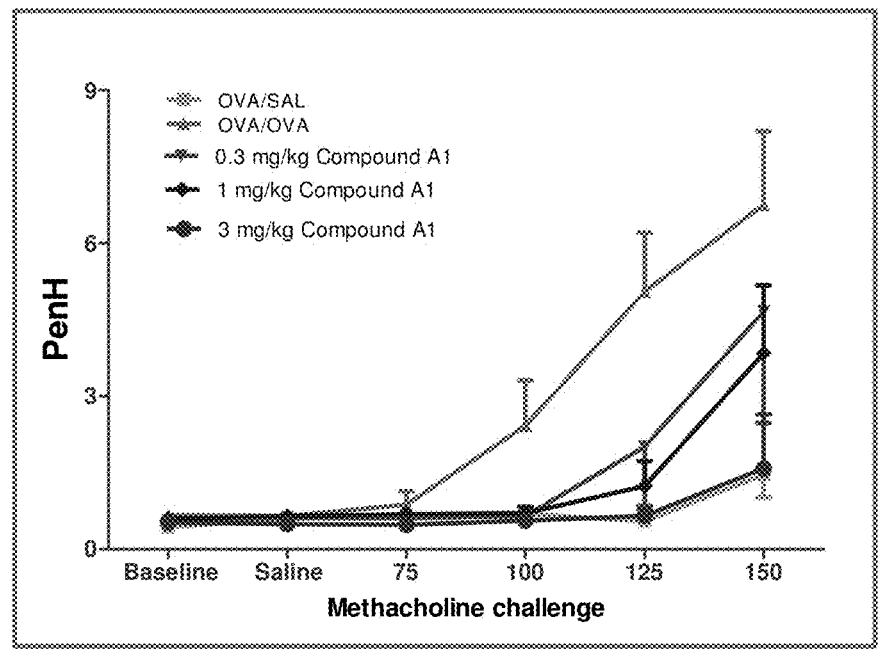
FIGS. 4A and 4B depict graphs of enhanced pause (Penh) or PEF/PIF (peak expiratory flow/peak inspiratory flow) ratio, respectively, in sensitized male guinea pigs following methacholine challenge and treatment with OVA/SAL or OVA/OVA or 0.3, 1, or 3 mg/kg Compound A1 according to the procedure in Assay 10A.
Figure 4B:
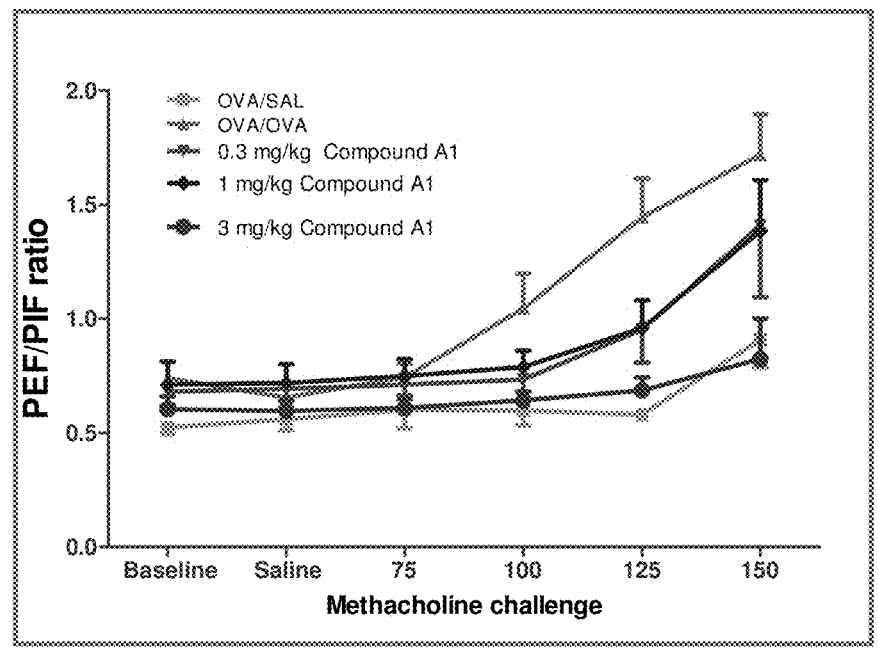

As depicted in the FIGS. 4A and 4B, Compound A1 caused a significant dose dependent reduction in airway hyperresponsiveness against methacholine challenge of sensitized Guinea pigs.

Figure 4C:
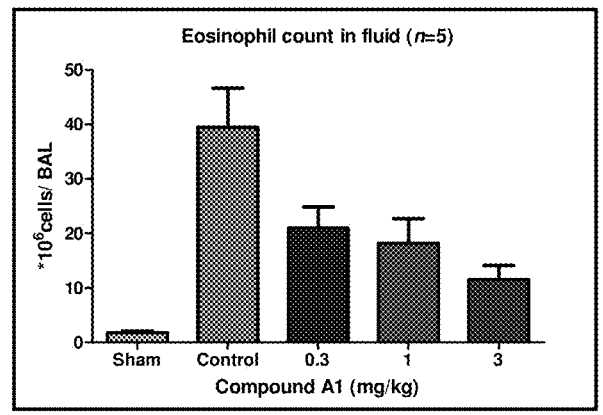
FIGS. 4C-4E depict bar graphs of eosinophil count in BALF, total cell count in BALF, and percentage eosinophils, respectively, in ovalbumin-sensitized male guinea pigs and treatment with 0, 0.3, 1, or 3 mg/kg Compound A1 according to the procedure in Assay 10A.
Figure 4D:
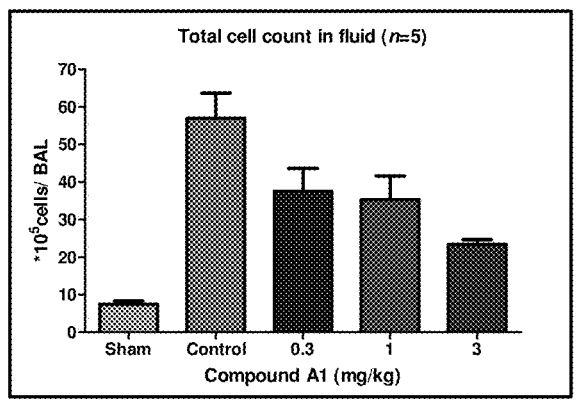
Figure 4E:
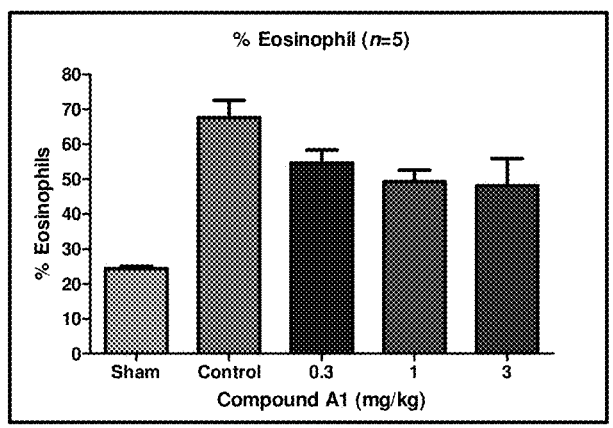

As depicted in the FIGS. 4C-4E, Compound A1 caused a significant dose dependent reduction in eosinophil infiltration into the bronchioalveolar lavage fluid of sensitized Guinea pigs.

Assay 10B: Murine Asthma Model

Airway inflammation and hyper-responsiveness (AHR) are hallmarks and distinguishing features of bronchial asthma. Provocation of pre-sensitized mice with the same allergen induces airway inflammation with preferential eosinophilic infiltration and, as a consequence, AHR. Pulmonary eosinophilia and airway remodelling in conjunction with altered neural control of airway tone and airway epithelial desquamation may contribute to AHR in asthma. After the quarantine period, based on their body weights, mice were randomized and divided into four groups (n=7). Tails were marked with an indelible marking pen for identification. On day 0, weights were recorded and animals were sensitized with 100 μg of Ovalbumin and 10 mg of alum solution (0.2 mL) intraperitoneally. On day 7 and day 14, the above sensitization protocol was repeated. Animals were observed for any signs of illness or reaction to the sensitization up to day 24 and recorded if any. On day 24, 25, and 26, after the treatment with test compound by oral gavage, 30 mins later animals were exposed to 10% w/v Ovalbumin challenge. Control and sham group animals were treated with 0.5% w/v methyl cellulose (vehicle). Sham control groups were sensitized with 10 mg of alum on day 0, 7 & 14 and exposed to saline solution with the same nebulization rate on day 24, 25 & 26. Forty eight hours after last OVA challenge, airway hyperresponsiveness was measured by whole body plethysmograph against cumulative doses of methacholine challenge (2.5, 10, 50 and 100 mg/ml), after measuring the airway response, blood samples and BAL fluid was collected. Samples were analysed for total cell count by using neubuear chamber under microscope and differential leukocyte count was done manually.

Figure 5A:
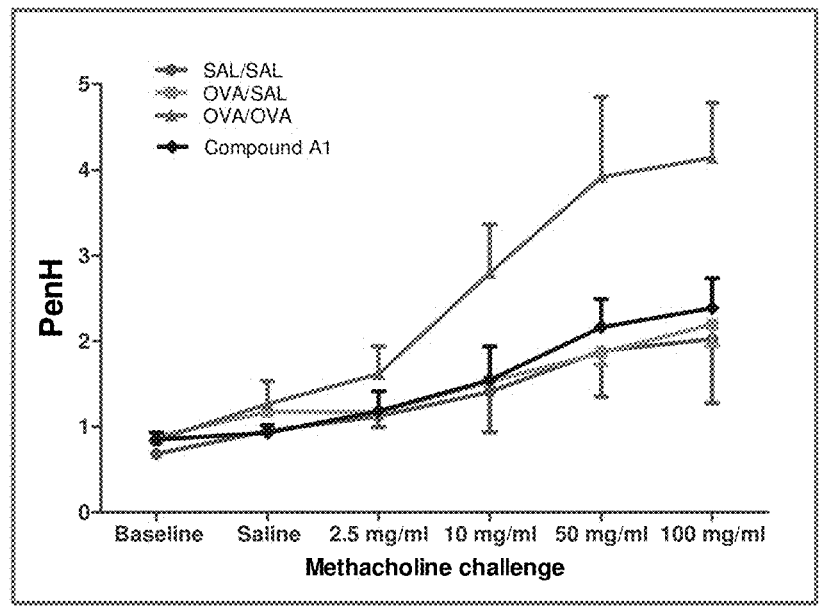
FIGS. 5A and 5B depict graphs of Penh) or PEF/PIF ratio, respectively, in ovalbumin-sensitized mice following methacholine challenge and treatment with SAL/SAL, OVA/SAL or OVA/OVA or 3 mg/kg Compound A1 according to the procedure in Assay 10B.
Figure 5B:
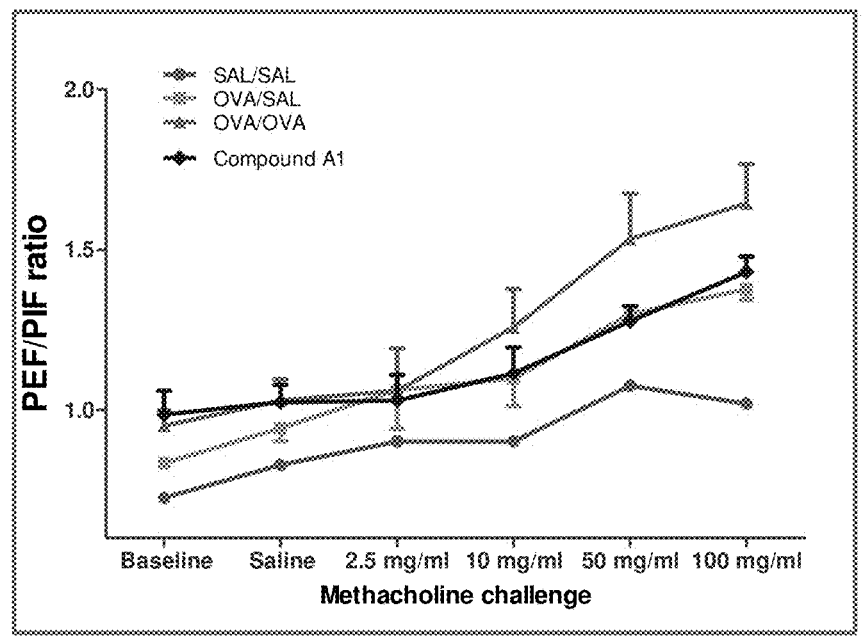

As depicted in the FIGS. 5A and 5B, Compound A1 at a dose of 3 mg/kg caused a significant reduction in airway hyperresponsiveness against methacholine challenge of ovalbumin sensitized mice.

Figure 5C:
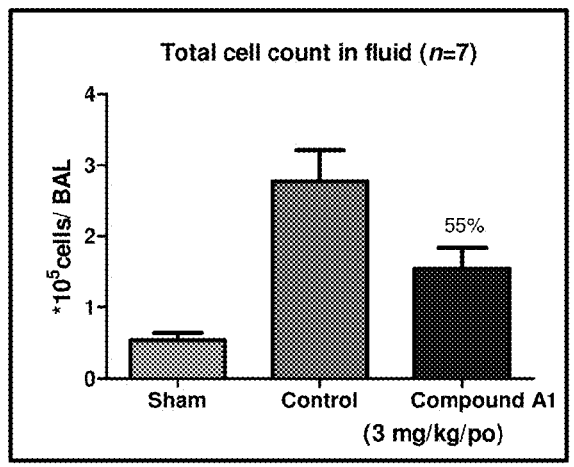
FIGS. 5C-5E depict bar graphs of eosinophil count in BALF, total cell count in BALF, and percentage eosinophils, respectively, in ovalbumin-sensitized mice and treated with 0 or 3 mg/kg Compound A1 according to the procedure in Assay 10B.
Figure 5D:
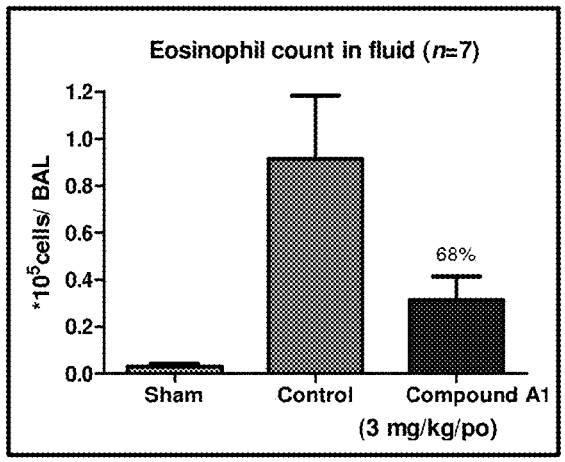
Figure 5E:
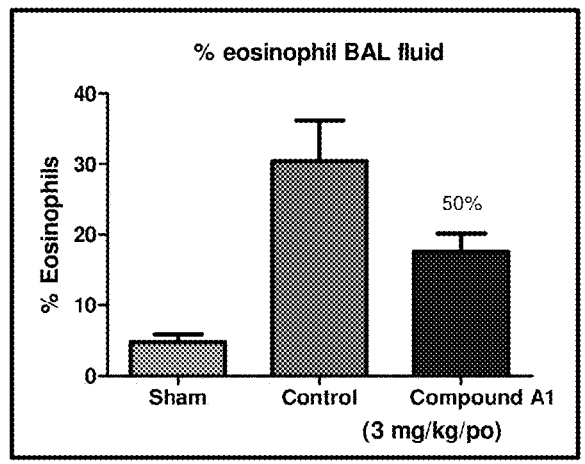
Figure 6A:
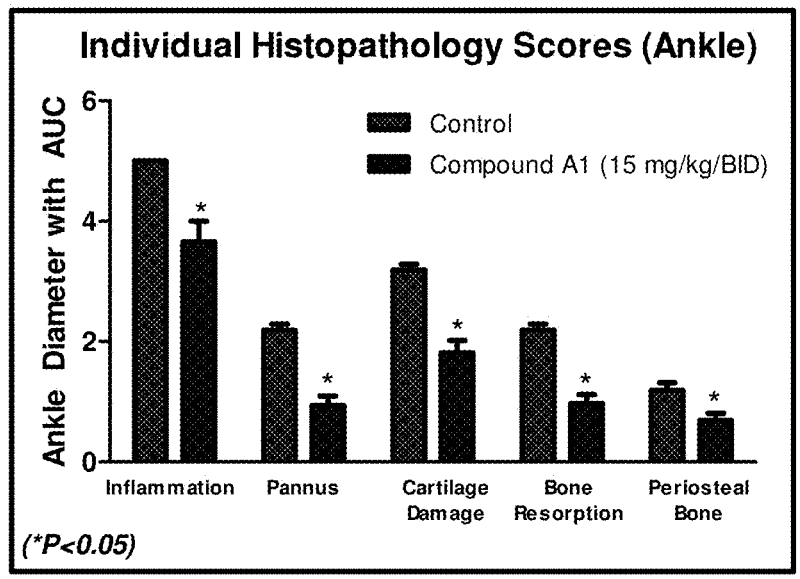
FIGS. 6A and 6B depict bar graphs of individual histopathological scores for ankle and knee, respectively, in collagen induced arthritis using Lewis rats treated with a control or 15 mg/kg/BID of compound A1 according to the procedure in Assay 11.
Figure 6B:
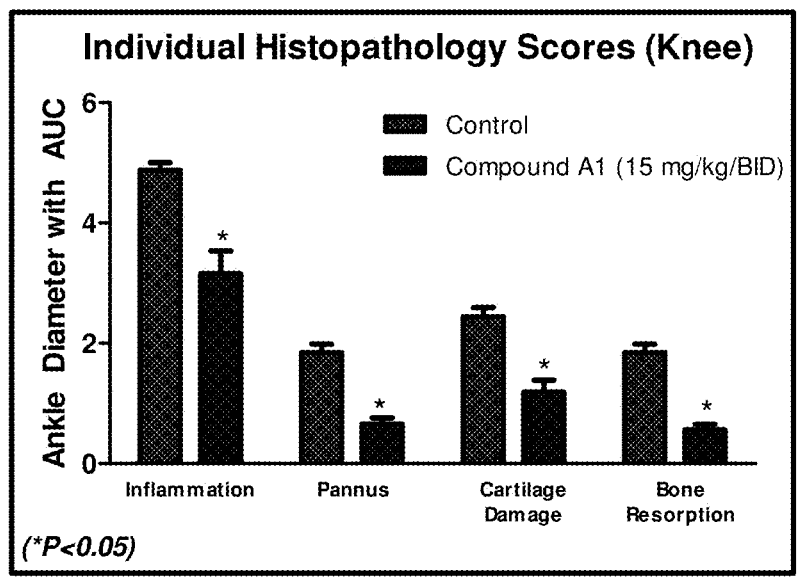
Figure 6C:
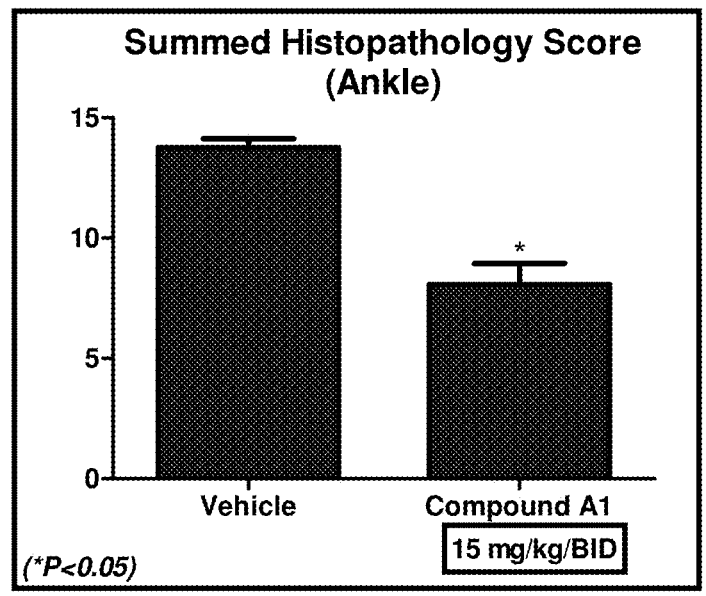
FIGS. 6C and 6D depict bar graphs of summed histopathological scores for ankle and knee, respectively, in collagen induced arthritis model using Lewis rats treated with vehicle or 15 mg/kg/BID of compound A1 according to the procedure in Assay 11.
Figure 6D:
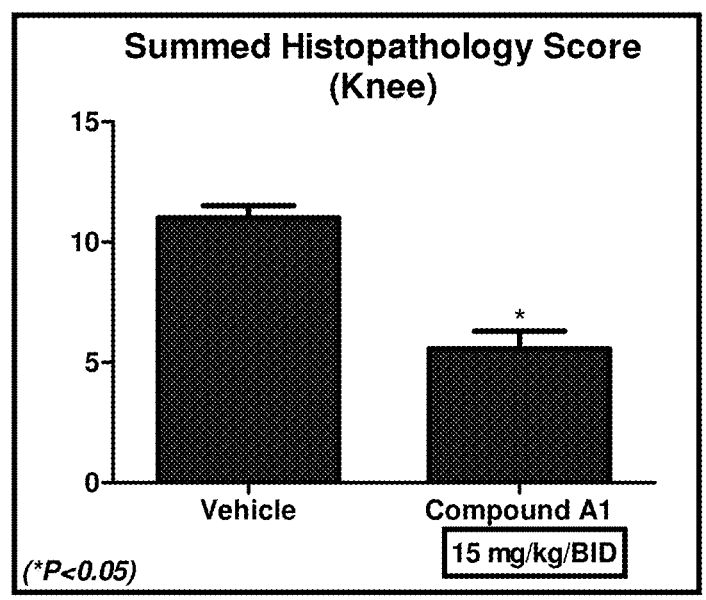

As depicted in the FIGS. 5C-5E, Compound A1 at a dose of 3 mg/kg caused a significant inhibition of eosinophil infiltration into the bronchioalveolar lavage fluid of ovalbumin sensitized mice.

Assay 11: Collagen Induced Arthritis in Lewis Rats

Female wistar rats were acclimatized for seven days prior to the start of the experiment and were randomly distributed to various groups based on their body weights. On day 0, animals were treated by intradermal injection of 500 μg of bovine collagen type II emulsified with complete Freund's adjuvant (IFA) containing MTB (4 mg/mL) delivered at the base of the tail. On day 7 after primary immunization, animals were treated by booster injection of 300 μg CII in incomplete Freund's adjuvant by intradermal injection at the base of the tail. Onset of arthritis in ankle joints usually became visually apparent between days 12 and 14. Animals were treated with test compound or vehicle (orally administered) from the day after onset of arthritis until end of the experiment (day 28) as a therapeutic group. Arthritis Scores were taken by visually examination for signs of joint inflammation regularly throughout the study period. Body weights and paw volumes, paw thickness has been taken on day 0, 3, 7, 10, 12, 14, 17 21, 24 and 28. On d28, at the end of the study, blood has been withdrawn at necropsy and processed to serum or plasma and all joints were taken and both fore paw and hind paws were fixed in 10% formalin for histopathology analysis after taking the small piece of tissue from each joint and stored at −80° C. for cytokine analysis in tissue homogenate. Clinical Scoring Criteria for Fore and Hind Paws: 0=normal; 1=one hind or fore paw joint affected or minimal diffuse erythema and swelling; 2=two hind or fore paw joints affected or mild diffuse erythema and swelling; 3=three hind or fore paw joints affected or moderate diffuse erythema and swelling; 4=marked diffuse erythema and swelling, or =four digit joints affected; 5=severe diffuse erythema and severe swelling entire paw, unable to flex digits.

Compound A1 dosed therapeutically in the rat CIA model demonstrates significant efficacy in reduction of knee and as well as ankle swelling.

Histological analysis of joints at study end demonstrates complete structural preservation at 15 mg/kg Compound A1. For comparison, a vehicle-dosed animal shows synovial (S) inflammation and significant evidence of bone resorption, pannus formation, and cartilage degradation and, as depicted in FIGS. 6A-6D, Compound A1 shows significant reduction in individual and summed histopathological scores for both knee and ankle.

Assay 12: Acute CSE Induced Cell Infiltration in Male Balb/c Mice

Animals (male Balb/c mice) are to be acclimatized for seven days prior to the start of the experiment Animals are to be randomly distributed to various groups based on their body weights. On day 1, mice are to be administered the test compound or vehicle by oral/intranasal route and after 1 hr the test compound administration the animals are to be anaesthetised with ether and cigarette smoke extract is to be administered by intranasal route in volume of 50 μl/mouse and repeated the CSE exposure to animals daily after the test compound administration for four days (d1 to d4). On day 5, 24 hours after last CSE exposure animals are to be exsanguinated under anesthesia, and the trachea is to be cannulated and the lungs are lavaged with 0.5-ml aliquots of heparinised PBS (1 unit/ml) four times through tracheal cannula (total volume 2 ml). BAL stored at 2-8° C. until assayed for total cell and differential leukocyte count. Bronchioalveolar fluid is to be centrifuged (500×g for 10 min) and the resulting cell pellet has to be resuspended in 0.5 ml of heparinised saline. The total number of white blood cells is to be determined in BAL fluid and blood using a blood cell counter and adjusted to $1\times10^6$ cell/ml. Differential cell count is to be calculated manually. Forty microliters of the cell suspension is to be centrifuged using cytospin 3 to prepare a cell smear. The cell smear is to be stained with a blood staining solution for differentiation and microscopically has to be observed to identify eosinophil according to their morphological characteristics. The number of each cell type among 300 white blood cells in the cell smear are to be determined and to be expressed as a percentage, and the number of neutrophils and macrophages in each BALf are to be calculated.

Assay 13: Sub-Chronic CSE Induced Cell Infiltration in Male Balb/c Mice

Animals (male Balb/c mice) are to be acclimatized for seven days prior to the start of the experiment Animals are to be randomly distributed to various groups based on their body weights. On day 1, animals are to be anaesthetised with ether and cigarette smoke extract is to be administered by intranasal route in volume of 50 μl/mouse and repeated the CSE exposure to animals daily for eight days (d1 to d8). On day 9, mice are to be administered by test compound or vehicle by oral/intranasal route and after 1 hr test compound administration animals are to be anaesthetised with ether and cigarette smoke extract is to be administered by intranasal route in volume of 50 μl/mouse and animals are to be exposed to CSE daily after the test compound administration for next three days (d9 to d11), on day 12, twenty four hours after last CSE exposure animals are to be exsanguinated under anesthesia, and the trachea is to be cannulated and the lungs are to be lavaged with 0.5-ml aliquots of heparinised PBS (1 unit/ml) four times through tracheal cannula (total volume 2 ml). BAL stored at 2-8° C. until assayed for total cell and differential leukocyte count. Bronchioalveolar fluid was centrifuged (500×g for 10 min) and the resulting cell pellet is to be resuspended in 0.5 ml of heparinised saline. The total numbers of white blood cells are to be determined in BAL fluid and blood using a blood cell counter and adjusted to $1\times10^6$ cell/ml. Differential cell count was calculated manually. Forty microliters of the cell suspension is to be centrifuged using cytospin 3 to prepare a cell smear. The cell smear is to be stained with a blood staining solution for differentiation and microscopically observed to identify eosinophil according to their morphological characteristics. The number of each cell type among 300 white blood cells in the cell smear has to be determined and expressed as a percentage, and the number of neutrophils and macrophages in each BALf are to be calculated.

Assay 14: Reversal of Corticosteroid Insensitivity in Cigarette Smoke Extract Induced Pulmonary Inflammation (COPD) Model Female Balb/c mice are to be acclimatized for seven days prior to the start of the experiment. Animals are then to be randomly distributed to various groups based on their body weights. On day 1, animals are to be anaesthetised with ether and cigarette smoke extract is to be administered by intranasal route in volume of 50 μl/mouse and animals are to be exposed to CSE daily for next five days (d1 to d6). On day 7, mice are to be administered by dexamethasone at 10 mg/kg by oral gavage and 60 mins later, mice are to be administered with CSE by intranasal route and it has to be repeated for next four days (d7 to d11). From day 9 to day 11, animals are to be administered by test compound or vehicle by oral/intranasal route and 30 mins after dexamethasone administration and 30 mins later animals are to be anaesthetised with ether and cigarette smoke extract is to be administered by intranasal route in volume of 50 μl/mouse and animals are to be exposed to CSE daily after the test compound administration for next two days (i.e. d9 to d11), on d12, twenty four hours after last CSE exposure animals are to be exsanguinated under anesthesia, and the trachea is to be cannulated and the lungs are to be lavaged with 0.5-ml aliquots of heparinised PBS (1 unit/ml) four times through tracheal cannula (total volume 2 ml). BAL has to be stored at 2-8° C. until assayed for total cell and differential leukocyte count. Bronchioalveolar fluid is to be centrifuged (500×g for 10 min) and the resulting cell pellet has to be resuspended in 0.5 ml of heparinised saline. The total number of white blood cells is to be determined in BAL fluid and blood using a blood cell counter and adjusted to $1\times10^6$ cell/ml. Differential cell count is to be calculated manually. Forty microliters of the cell suspension is to be centrifuged using cytospin 3 to prepare a cell smear. The cell smear is to be stained with a blood staining solution for differentiation and microscopically has to be observed to identify eosinophil according to their morphological characteristics. The number of each cell type among 300 white blood cells in the cell smear are to be determined and will be expressed as a percentage, and the number of neutrophils and macrophages in each BAL fluid are to be calculated.

Assay 15: Acute Cigarette Smoke Induced Cell Infiltration in Male Balb/c Mice

Animals (male Balb/c mice) are to be acclimatized for seven days prior to the start of the experiment. Animals are then to be randomly distributed to various groups based on their body weights. On day 1, mice is to be administered test compound or vehicle by oral/intranasal route and after 1 hr test compound administration animals are to be placed in whole body exposure box. On day 1 and d2 mice are exposed to the mainstream smoke of 6 cigarettes and of 8 cigarettes on day 3, and of 10 cigarettes on day 4. Exposure to the smoke of each cigarette lasts for 10 min (cigarette are to be completely burned in the first two minutes and followed by an air flow with animal ventilator and next 20 min exposure with fresh room air. After every second cigarette an additional break of 20 min with exposure to fresh room air is to be conducted. Control animals are to be exposed to room air chamber. From day 1 to d4 animals are administered by test compound either oral or intranasal route. On day 5, 24 hours after last cigarette smoke (CS) exposure animals are exsanguinated under anesthesia, and the trachea is to be cannulated and the lungs are lavaged with 0.5-ml aliquots of heparinised PBS (1 unit/ml) four times through tracheal cannula (total volume 2 ml). Bronchioalveolar (BAL) collected is to be stored at 2-8° C. until assayed for total cell and differential leukocyte count. BAL fluid is to be centrifuged (500×g for 10 min) and the resulting cell pellet is resuspended in 0.5 ml of heparinised saline. The total number of white blood cells is to be determined in BAL fluid and blood using a blood cell counter and adjusted to $1\times10^6$ cell/ml. Differential cell count is calculated manually. Forty microliters of the cell suspension is centrifuged using cytospin 3 to prepare a cell smear. The cell smear is stained with a blood staining solution for differentiation and microscopically observed to identify eosinophil according to their morphological characteristics. The number of each cell type among 300 white blood cells in the cell smear are to be determined and expressed as a percentage, and the number of neutrophils and macrophages in each BAL fluid are to be calculated.

Figure 7A:
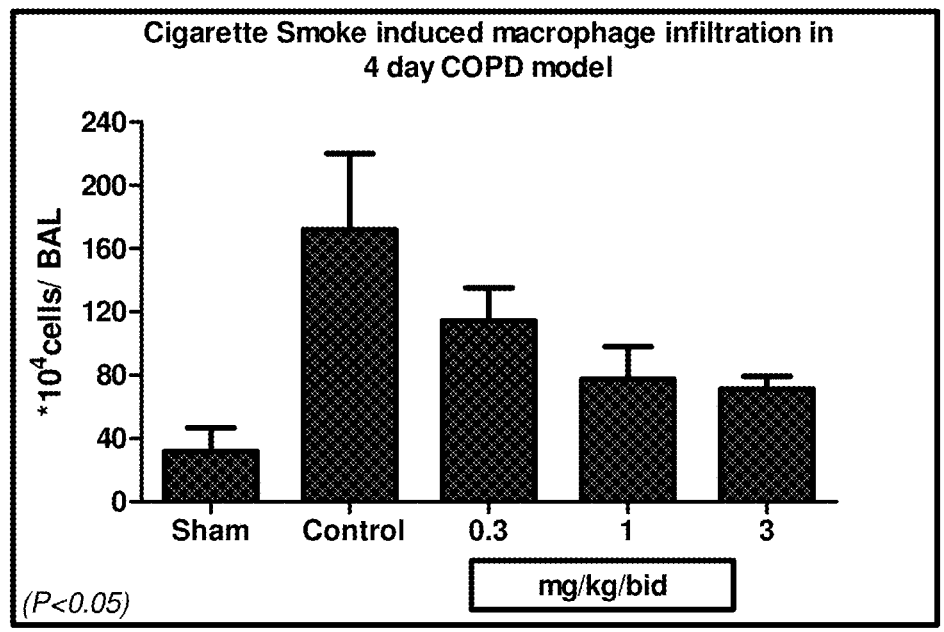
FIGS. 7A and 7B depict bar graphs of macrophage and neutrophil cell counts, respectively, in BALF following administration of 0.3, 1, or 3 mg/kg/BID of Compound A1 in male Balb/c mice in a cigarette smoke induced cell infiltration model as described in Assay 15.
Figure 7B:
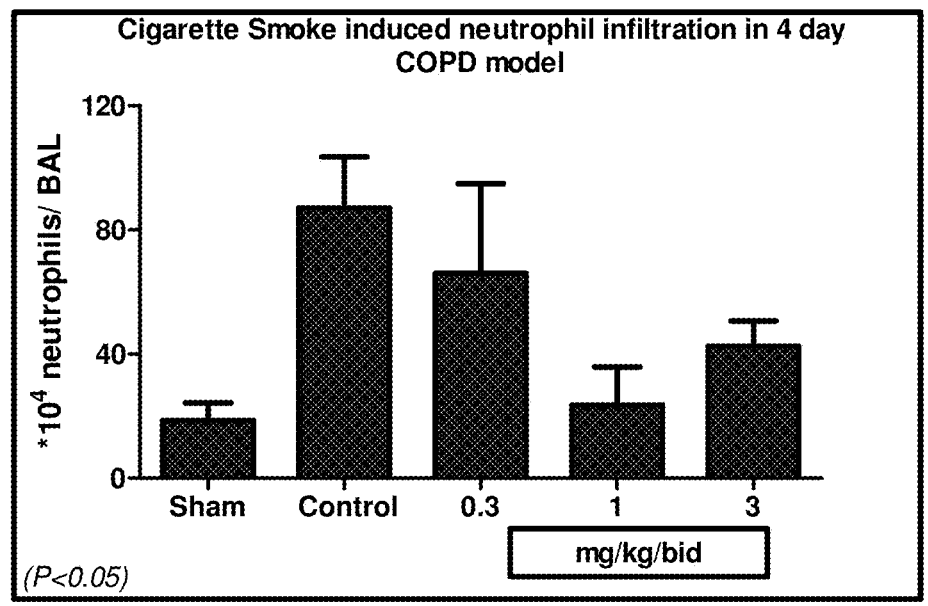

Results:

As depicted in FIGS. 7A and 7B, Compound A1 reduced macrophages and neutrophil infiltration into BALF thereby indicating a therapeutic role in chronic obstructive pulmonary diseases Assay 16: Ovalbumin-Induced Nasal Eosinophil and Neutrophil Accumulation in Mice Animals (mice) are to be acclimatized for seven days prior to the start of the experiment. Animals are then to be randomly distributed to various groups based on their body weights. Animals are to be immunized with OVA (40 μg/kg i.p.) on day 1 and 5. In order to elicit local inflammatory responses in the nose, mice are to be repeatedly challenged intra-nasally (10 μL/per nostril) on days 12-19 with OVA (3% OVA in saline). On day 19 non-fasted mice are to be dosed intra-nasally (10 μL/nostril) with either vehicle or test compound 2 hours before to the start of the final OVA challenge. Two hrs later, each animal is to be received a final intranasal OVA (3%) challenge). After a further 8 hr, each animal is to be anaesthetized and nasal lavage is to be carried out by instilling 1 ml of PBS into the posterior nares via a rostrally implanted tracheal cannula extending to a position that is approximately 1 mm before the posterior nares. This procedure has to be repeated to give a yield of approximately 2 ml of lavage fluid. Total cell numbers in the nasal lavage fluid samples are to be measured using a haemocytometer. Cytospin smears of the nasal lavage fluid samples are to be prepared by centrifugation at 1200 rpm for 2 min at RT and stained using a Diff-Quik stain system (Dade Behring) for differential cell counts. Cells are to be counted using oil immersion microscopy.

Assay 17: Poly-LC-Induced Cell Accumulation in Mice

Specific pathogen-free A/J mice (males, 5 weeks old) are to be acclimatized for seven days prior to the start of the experiment. Animals are then to be randomly distributed to various groups based on their body weights Animals are to be administered with poly (1:C)-LMW (poly-IC; 1 mg/mL, 40 μL) intranasally twice daily for 3 days under anaesthesia with 3% isoflurane Animals are to be treated with test compound by intra-nasally (35 μL of solution in 50% DMSO/PBS) 2 hr before each poly-1:C treatment. Twenty four hr after the last poly-1:C challenge, animals are to be anesthetized, the trachea has to be cannulated and BALF is to be collected. The concentrations of alveolar macrophages and neutrophils in BALF are to be determined by using a blood cell counter and adjusted to $1\times10^6$ cell/ml. Differential cell count is calculated manually. Forty microliters of the cell suspension is centrifuged using cytospin 3 to prepare a cell smear. The cell smear is stained with a blood staining solution for differentiation and microscopically observed to identify eosinophil according to their morphological characteristics. The number of each cell type among 300 white blood cells in the cell smear are to be determined and expressed as a percentage, and the number of neutrophils and macrophages in each BAL fluid are to be calculated.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as described above. It is intended that the appended claims define the scope of the invention and that methods and structures within the scope of these claims and their equivalents be covered thereby.

Pharmaceutical Composition of Compound A1

Example I

The capsules described below containing 5 or 10 mg of Compound A1 are prepared.

| Ingredients | % w/w |
| --- | --- |
| Compound A1 | 4.5 |
| Microcrystalline cellulose (Avicel PH102) | 83.8 |
| Hydroxypropyl cellulose (Klucel LF) | 4.5 |
| Purified Water | q.s |
| Low substituted hydroxylpropyl cellulose (L-HPC; LH-11) | 5.9 |
| Talc | 0.3 |
| Colloidal silicon dioxide (Aerosil-200) | 0.3 |
| Magnesium stearate | 0.6 |

Example II

The capsules described below containing 25, 50, or 100 mg of Compound A1 are prepared.

| Ingredients | % w/w |
| --- | --- |
| Compound A1 | 22.7 |
| Microcrystalline cellulose (Avicel PH102) | 67.2 |
| Hydroxypropyl cellulose (Klucel LF) | 3.4 |
| Purified Water | q.s |
| Low substituted hydroxylpropyl cellulose (L-HPC; LH-11) | 5.7 |
| Talc | 0.2 |
| Colloidal silicon dioxide (Aerosil-200) | 0.2 |
| Magnesium stearate | 0.6 |

All publications and patent and/or patent applications cited in this application are herein incorporated by reference to the same extent as if each individual publication or patent application was specifically and individually indicated to be incorporated herein by reference.

What is claimed is:

1. A composition comprising (S)-2-(1-(9H-purin-6-ylamino)propyl)-3-(3-fluorophenyl)-4H-chromen-4-one or a pharmaceutically acceptable salt thereof, wherein the composition is substantially free of (R)-2-(1-(9H-purin-6-ylamino)propyl)-3-(3-fluorophenyl)-4H-chromen-4-one and pharmaceutically acceptable salts thereof.

2. A composition comprising (S)-2-(1-(9H-purin-6-ylamino)propyl)-3-(3-fluorophenyl)-4H-chromen-4-one, wherein the composition is substantially free of (R)-2-(1-(9H-purin-6-ylamino)prop yl)-3-(3-fluorophenyl)-4H-chromen-4-one.

3. A composition comprising (S)-2-(1-(9H-purin-6-ylamino)propyl)-3-(3-fluorophenyl)-4H-chromen-4-one or a pharmaceutically acceptable salt thereof, wherein the composition has an enantiomeric excess greater than about 90% relative to (R)-2-(1-(9H-purin-6-ylamino)propyl)-3-(3-fluorophenyl)-4H-chromen-4-one.

4. A composition comprising (S)-2-(1-(9H-purin-6-ylamino)propyl)-3-(3-fluorophenyl)-4H-chromen-4-one, wherein the composition has an enantiomeric excess greater than about 90% relative to (R)-2-(1-(9H-purin-6-ylamino)propyl)-3-(3-fluorophenyl)-4H-chromen-4-one %.

5. A pharmaceutical composition comprising (S)-2-(1-(9H-purin-6-ylamino)propyl)-3-(3-fluorophenyl)-4H-chromen-4-one or a pharmaceutically acceptable salt thereof and at least one pharmaceutically acceptable carrier, wherein the composition is substantially free of (R)-2-(1-(9H-purin-6-ylamino)propyl)-3-(3-fluorophenyl)-4H-chromen-4-one and pharmaceutically acceptable salts thereof.

6. A pharmaceutical composition comprising (S)-2-(1-(9H-purin-6-ylamino)propyl)-3-(3-fluorophenyl)-4H-chromen-4-one and at least one pharmaceutically acceptable carrier, wherein the composition is substantially free of (R)-2-(1-(9H-purin-6-ylamino)propyl)-3-(3-fluorophenyl)-4H-chromen-4-one.

7. A pharmaceutical composition comprising (S)-2-(1-(9H-purin-6-ylamino)propyl)-3-(3-fluorophenyl)-4H-chromen-4-one or a pharmaceutically acceptable salt thereof and at least one pharmaceutically acceptable carrier, wherein the composition has an enantiomeric excess greater than about 90% relative to (R)-2-(1-(9H-purin-6-ylamino)propyl)-3-(3-fluorophenyl)-4H-chromen-4-one.

8. A pharmaceutical composition comprising (S)-2-(1-(9H-purin-6-ylamino)propyl)-3-(3-fluorophenyl)-4H-chromen-4-one and at least one pharmaceutically acceptable carrier, wherein the composition has an enantiomeric excess greater than about 90% relative to (R)-2-(1-(9H-purin-6-ylamino)propyl)-3-(3-fluorophenyl)-4H-chromen-4-one.

9. The composition of claim 3, wherein the composition has an enantiomeric excess of (S)-2-(1-(9H-purin-6-ylamino)propyl)-3-(3-fluorophenyl)-4H-chromen-4-one or a pharmaceutically acceptable salt thereof greater than about 95%.

10. The composition of claim 3, wherein the composition has an enantiomeric excess of (S)-2-(1-(9H-purin-6-ylamino)propyl)-3-(3-fluorophenyl)-4H-chromen-4-one or a pharmaceutically acceptable salt thereof greater than about 98%.

11. The composition of claim 3, wherein the composition has an enantiomeric excess of (S)-2-(1-(9H-purin-6-ylamino)propyl)-3-(3-fluorophenyl)-4H-chromen-4-one or a pharmaceutically acceptable salt thereof greater than about 99%.

12. The composition of claim 4, wherein the composition has an enantiomeric excess of (S)-2-(1-(9H-purin-6-ylamino)propyl)-3-(3-fluorophenyl)-4H-chromen-4-one greater than about 95%.

13. The composition of claim 4, wherein the composition has an enantiomeric excess of (S)-2-(1-(9H-purin-6-ylamino)propyl)-3-(3-fluorophenyl)-4H-chromen-4-one greater than about 98%.

14. The composition of claim 4, wherein the composition has an enantiomeric excess of (S)-2-(1-(9H-purin-6-ylamino)propyl)-3-(3-fluorophenyl)-4H-chromen-4-one greater than about 99%.

15. The pharmaceutical composition of claim 7, wherein the composition has an enantiomeric excess of (S)-2-(1-(9H-purin-6-ylamino)propyl)-3-(3-fluorophenyl)-4H-chromen-4-one or a pharmaceutically acceptable salt thereof greater than about 95%.

16. The pharmaceutical composition of claim 7, wherein the composition has an enantiomeric excess of (S)-2-(1-(9H-purin-6-ylamino)propyl)-3-(3-fluorophenyl)-4H-chromen-4-one or a pharmaceutically acceptable salt thereof greater than about 98%.

17. The pharmaceutical composition of claim 7, wherein the composition has an enantiomeric excess of (S)-2-(1-(9H-purin-6-ylamino)propyl)-3-(3-fluorophenyl)-4H-chromen-4-one or a pharmaceutically acceptable salt thereof greater than about 99%.

18. The pharmaceutical composition of claim 8, wherein the composition has an enantiomeric excess of (S)-2-(1-(9H-purin-6-ylamino)propyl)-3-(3-fluorophenyl)-4H-chromen-4-one greater than about 95%.

19. The pharmaceutical composition of claim 8, wherein the composition has an enantiomeric excess of (S)-2-(1-(9H-purin-6-ylamino)propyl)-3-(3-fluorophenyl)-4H-chromen-4-one greater than about 98%.

20. The pharmaceutical composition of claim 8, wherein the composition has an enantiomeric excess of (S)-2-(1-(9H-purin-6-ylamino)propyl)-3-(3-fluorophenyl)-4H-chromen-4-one greater than about 99%.

21. A method of inhibiting a catalytic activity of a PI3 δ kinase present in a cell, comprising contacting the cell with an effective amount of a composition of claim 1.

22. A method of inhibiting a catalytic activity of a PI3 γ kinase present in a cell, comprising contacting the cell with an effective amount of a composition of claim 1.

23. A method of inhibiting a catalytic activity of a PI3 δ kinase and PI3 γ kinase present in a cell, comprising contacting the cell with an effective amount of a composition of claim 1.

24. The method of claim 21, wherein the inhibition takes place in a cell, wherein the cell is in a subject suffering from leukemia.

25. A method of ameliorating leukemia, the method comprising administering an effective amount of a composition of claim 1 to a patient in need thereof.

26. The method of claim 25, wherein the leukemia is acute lymphocytic leukemia, acute lymphoblastic leukemia, chronic lymphocytic leukemia (CLL), or acute myeloid leukemia (AML).

27. A method of inhibiting a catalytic activity of a PI3 δ kinase present in a cell, comprising contacting the cell with an effective amount of a pharmaceutical composition of claim 5.

28. A method of inhibiting a catalytic activity of a PI3 γ kinase present in a cell, comprising contacting the cell with an effective amount of a pharmaceutical composition of claim 5.

29. A method of inhibiting a catalytic activity of a PI3 δ kinase and PI3 γ kinase present in a cell, comprising contacting the cell with an effective amount of a pharmaceutical composition of claim 5.

30. The method of claim 27, wherein the inhibition takes place in a cell, wherein the cell is in a subject suffering from leukemia.

31. A method of ameliorating leukemia, the method comprising administering an effective amount of a pharmaceutical composition of claim 5 to a patient in need thereof.

32. The method of claim 31, wherein the leukemia is acute lymphocytic leukemia, acute lymphoblastic leukemia, chronic lymphocytic leukemia (CLL), or acute myeloid leukemia (AML).

* * * * *